(12) United States Patent
Wang et al.

(10) Patent No.: US 9,793,477 B2
(45) Date of Patent: Oct. 17, 2017

(54) MULTINOZZLE EMITTER ARRAYS FOR ULTRAHIGH-THROUGHPUT NANOELECTROSPRAY MASS SPECTROMETRY

(71) Applicant: The Regents of the University of California, Oakland, CA (US)

(72) Inventors: Daojing Wang, Moraga, CA (US); Pan Mao, Fremont, CA (US); Hung-Ta Wang, Tuscaloosa, AL (US); Peidong Yang, Kensington, CA (US)

(73) Assignee: The Regents of The University of California, Oakland, CA (US)

( * ) Notice: Subject to any disclaimer, the term of this patent is extended or adjusted under 35 U.S.C. 154(b) by 114 days.

(21) Appl. No.: 14/137,840

(22) Filed: Dec. 20, 2013

(65) Prior Publication Data
US 2014/0110661 A1    Apr. 24, 2014

Related U.S. Application Data

(63) Continuation of application No. PCT/US2012/045082, filed on Jun. 29, 2012.
(Continued)

(51) Int. Cl.
*H01L 49/00* (2006.01)
*B01D 59/44* (2006.01)
(Continued)

(52) U.S. Cl.
CPC .......... *H01L 49/00* (2013.01); *H01J 49/0018* (2013.01); *H01J 49/167* (2013.01);
(Continued)

(58) Field of Classification Search
CPC ................... H01J 49/00; H01J 49/0018; H01J 49/167; H01J 49/0004; H01J 49/0013; H01J 49/04;
(Continued)

(56) References Cited

U.S. PATENT DOCUMENTS 5,993,633 A * 11/1999 Smith ............... G01N 27/44717
204/450
6,630,835 B2    10/2003 Cheng et al.
(Continued)

OTHER PUBLICATIONS

International Search Report and Written Opinion for International Application No. PCT/US2012/045082 dated Sep. 24, 2012.
(Continued)

*Primary Examiner* — Cheung Lee
*Assistant Examiner* — Stephen C Smith
(74) *Attorney, Agent, or Firm* — Lawrence Berkeley National Laboratory

(57) ABSTRACT

The present invention provides for a structure comprising a plurality of emitters, wherein a first nozzle of a first emitter and a second nozzle of a second emitter emit in two directions that are not or essentially not in the same direction; wherein the walls of the nozzles and the emitters form a monolithic whole. The present invention also provides for a structure comprising an emitter with a sharpened end from which the emitter emits; wherein the emitters forms a monolithic whole. The present invention also provides for a fully integrated separation of proteins and small molecules on a silicon chip before the electrospray mass spectrometry analysis.

14 Claims, 20 Drawing Sheets

Related U.S. Application Data

(60) Provisional application No. 61/502,762, filed on Jun. 29, 2011.

(51) Int. Cl.

| G01N 30/72 | (2006.01) |
|---|---|
| B01D 3/00 | (2006.01) |
| H01J 49/04 | (2006.01) |
| H01J 49/00 | (2006.01) |
| H01J 49/16 | (2006.01) |
| B01L 3/00 | (2006.01) |

(52) U.S. Cl.
CPC ............. *B01D 59/44* (2013.01); *B01L 3/5027* (2013.01); *G01N 30/72* (2013.01); *G01N 30/7206* (2013.01); *H01J 49/04* (2013.01)

(58) Field of Classification Search
CPC . G01N 30/72; H01L 49/0004; H01L 49/0013; B01D 59/44
See application file for complete search history.

(56) References Cited

U.S. PATENT DOCUMENTS

| 6,962,831 | B2 | 11/2005 | Najafi et al. | |
|---|---|---|---|---|
| 7,105,812 | B2* | 9/2006 | Zhao | B01L 3/0268 250/281 |
| 7,384,600 | B2* | 6/2008 | Burns | B01F 9/0001 422/64 |
| 7,970,318 | B2 | 6/2011 | Iwamatsu et al. | |
| 8,022,361 | B2* | 9/2011 | Wang | B82Y 15/00 239/548 |
| 9,006,648 | B2* | 4/2015 | Ramsey | B05B 5/025 250/282 |
| 2002/0084290 | A1 | 7/2002 | Materna | |
| 2004/0067578 | A1* | 4/2004 | Axelsson | B05B 5/0255 435/287.2 |
| 2005/0133713 | A1* | 6/2005 | Brennen | B81B 1/00 250/288 |
| 2006/0113463 | A1* | 6/2006 | Rossier | H01J 49/167 250/288 |
| 2009/0130745 | A1* | 5/2009 | Williams | B01L 3/5027 435/287.2 |
| 2009/0266516 | A1 | 10/2009 | Jewell-Larson et al. | |
| 2010/0075428 | A1* | 3/2010 | Wang | H01J 49/165 436/86 |
| 2011/0147576 | A1* | 6/2011 | Wouters | H01J 49/167 250/282 |
| 2013/0014567 | A1* | 1/2013 | Bunner | B01L 3/502707 73/61.55 |
| 2014/0047907 | A1* | 2/2014 | Murphy | H01J 49/0431 73/61.55 |

OTHER PUBLICATIONS

Overstolz, T. et al., A Clean Wafer-Scale Chip-Release Process without Dicing Based on Vapor Phase Etching. Presented at the 17th IEEE International Conference on Micro Electro Mechanical Systems, Jan. 25-29, 2004, Maaastricht, The Netherlands. Published in the Technical Digest, ISBN 0-7803-8265-X, pp. 717-720.
Pan Mao et al., Multinozzle Emitter Arrays for Nanoelectrospray Mass Spectrometry, Anal. Chem. 2011, 83, 6082-6089.
Schultz, G. A.; Corso, T. N.; Prosser, S. J.; Zhang, S.; A Fully Integrated Monolithic Microchip Electrospray Device for Mass Spectrometry; Anal. Chem. 2000, 72, 4058-4063.
Gibson, G. T.; Mugo, S. M.; Oleschuk, R. D.; Nanoelectrospray emitters: Trends and perspective; Mass Spectrom. Rev. 2009, 28, 918-936.
Kelly, R. T.; Page, J. S.; Zhao, R.; Qian, W. J.; Mottaz, H. M.; Tang, K.; Smith, R. D.; Capillary-Based Multi Nanoelectrospray Emitters: Improvements in Ion Transmission Efficiency and Implementation with Capillary Reversed-Phase LC-ESI-MS; Anal. Chem. 2008, 80, 143-149.
Su, S.; Gibson, G. T.; Mugo, S. M.; Marecak, D. M.; Oleschuk, R. D.; Microstructured Photonic Fibers as Multichannel Electrospray Emitters; Anal. Chem. 2009, 81, 7281-7287.
Xue, Q.; Foret, F.; Dunayevskiy, Y. M.; Zavracky, P. M.; McGruer, N. E.; Karger, B. L.; Multichannel Microchip Electrospray Mass Spectrometry; Anal. Chem. 1997, 69, 426-430.
Liu, H.; Felten, C.; Xue, Q.; Zhang, B.; Jedrzejewski, P.; Karger, B. L.; Foret, F.; Development of Multichannel Devices with an Array of Electrospray Tips for High-Throughput Mass Spectrometry; Anal. Chem. 2000, 72, 3303-3310.
Dayon, L.; Abonnenc, M.; Prudent, M.; Lion, N.; Girault, H. H.; Multitrack electrospray chips; J. Mass Spectrom. 2006, 41, 1484-1490.
Moini, M.; Jiang, L.; Bootwala, S.; High-throughput analysis using gated multi-inlet mass spectrometry; Rapid Commun. Mass Spectrom. 2011, 25, 789-794.
Kim, W.; Guo, M.; Yang, P.; Wang, D.; Microfabricated Monolithic Multinozzle Emitters for Nanoelectrospray Mass Spectrometry; Anal. Chem. 2007, 79, 3703-3707.
Marginean, I.; Kelly, R. T.; Page, J. S.; Tang, K.; Smith, R. D.; Electrospray Characteristic Curves: In Pursuit of Improved Performance in the Nanoflow Regime; Anal. Chem. 2007, 79, 8030-8036.
Kelly, R. T.; Tang, K; Irimia, D.; Toner, M.; Smith, R. D.; Elastomeric Microchip Electrospray Emitter for Stable Cone-Jet Mode Operation in the Nanoflow Regime; Anal. Chem. 2008, 80, 3824-3831.
Koster, S.; Verpoorte, E., A decade of microfluidic analysis coupled with electrospray mass spectrometry: an overview. Lab Chip 2007, 7, (11), 1394-412.
Licklider, L.; Wang, X. Q.; Desai, A.; Tai, Y. C.; Lee, T. D., A micromachined chip-based electrospray source for mass spectrometry. Anal Chem 2000, 72, (2), 367-75.
Yang, Y.; Kameoka, J.; Wachs, T.; Henion, J. D.; Craighead, H. G., Quantitative mass spectrometric determination of methylphenidate concentration in urine using an electrospray ionization source integrated with a polymer microchip. Anal Chem 2004, 76, (9), 2568-74.
Kim, J. S.; Knapp, D. R., Microfabricated PDMS multichannel emitter for electrospray ionization mass spectrometry. J Am Soc Mass Spectrom 2001, 12, (4), 463-9.
Schilling, M.; Nigge, W.; Rudzinski, A.; Neyer, A.; Hergenroder, R., A new onchip ESI nozzle for coupling of MS with microfluidic devices. Lab Chip 2004, 4, (3), 220-4.
Le Gac, S.; Cren-Olive, C.; Rolando, C.; Arscott, S., A novel nib-like design for microfabricated nanospray tips. J Am Soc Mass Spectrom 2004, 15, (3), 409-12.
Bocanegra, R.; Galán, D.; Márquez, M.; Loscertales, I. G.; Barrero, A., Multiple electrosprays emitted from an array of holes. J. Aerosol Sci. 2005, 36, 1387-1399.
Deng, W. W.; Klemic, J. F.; Li, X. H.; Reed, M. A.; Gomez, A., Increase of electrospray throughput using multiplexed microfabricated sources for the scalable generation of monodisperse droplets. J. Aerosol Sci. 2006, 37, 696-714.
Tatemoto, Y.; Ishikawa, R.; Takeuchi, M.; Takeshita, T.; Noda, K; Okazaki, T., An electrospray method using a multi-capillary nozzle emitter. Chem. Eng. Technol. 2007, 30, (9), 1274-1279.

\* cited by examiner

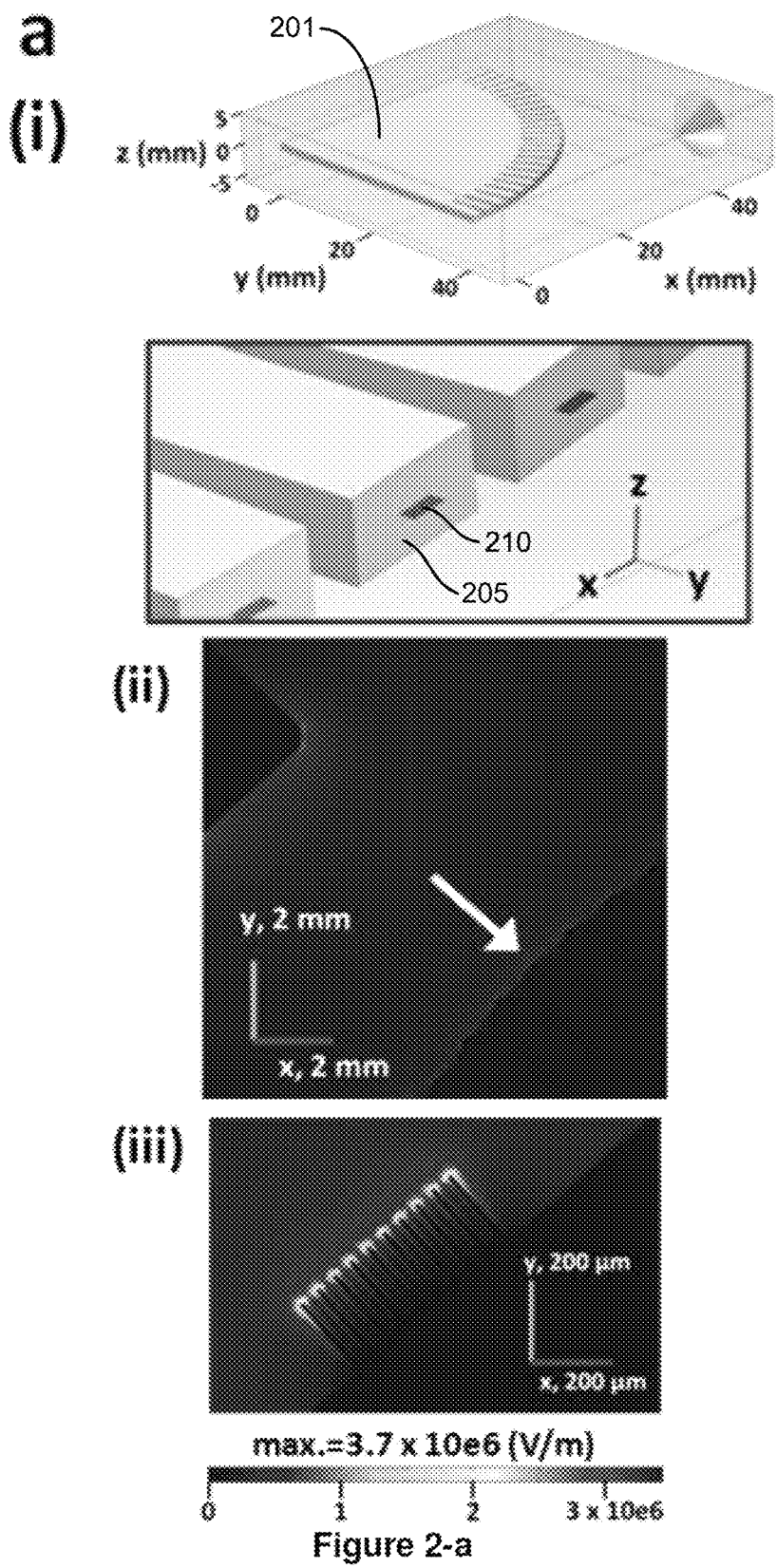
Figure 2-a

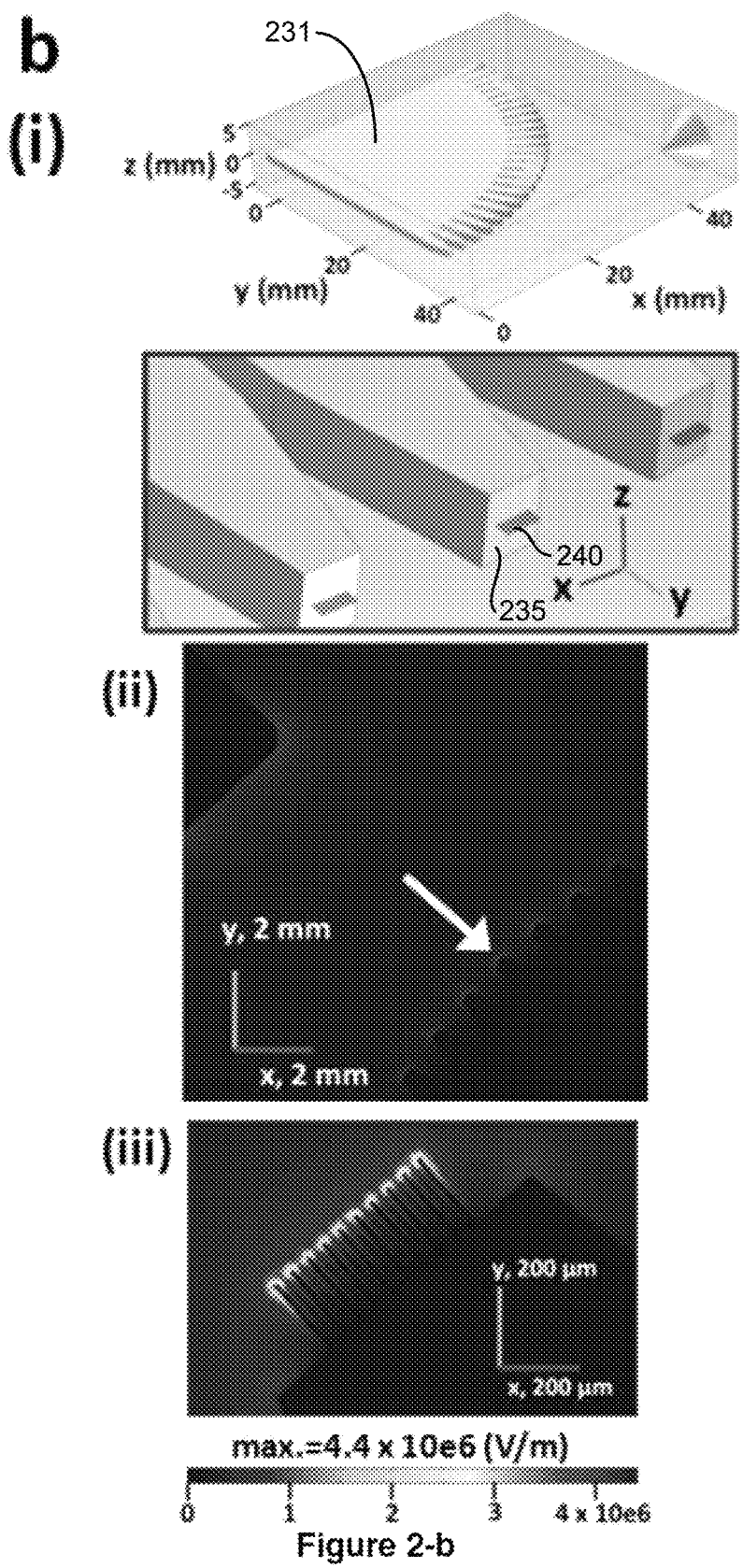
Figure 2-b

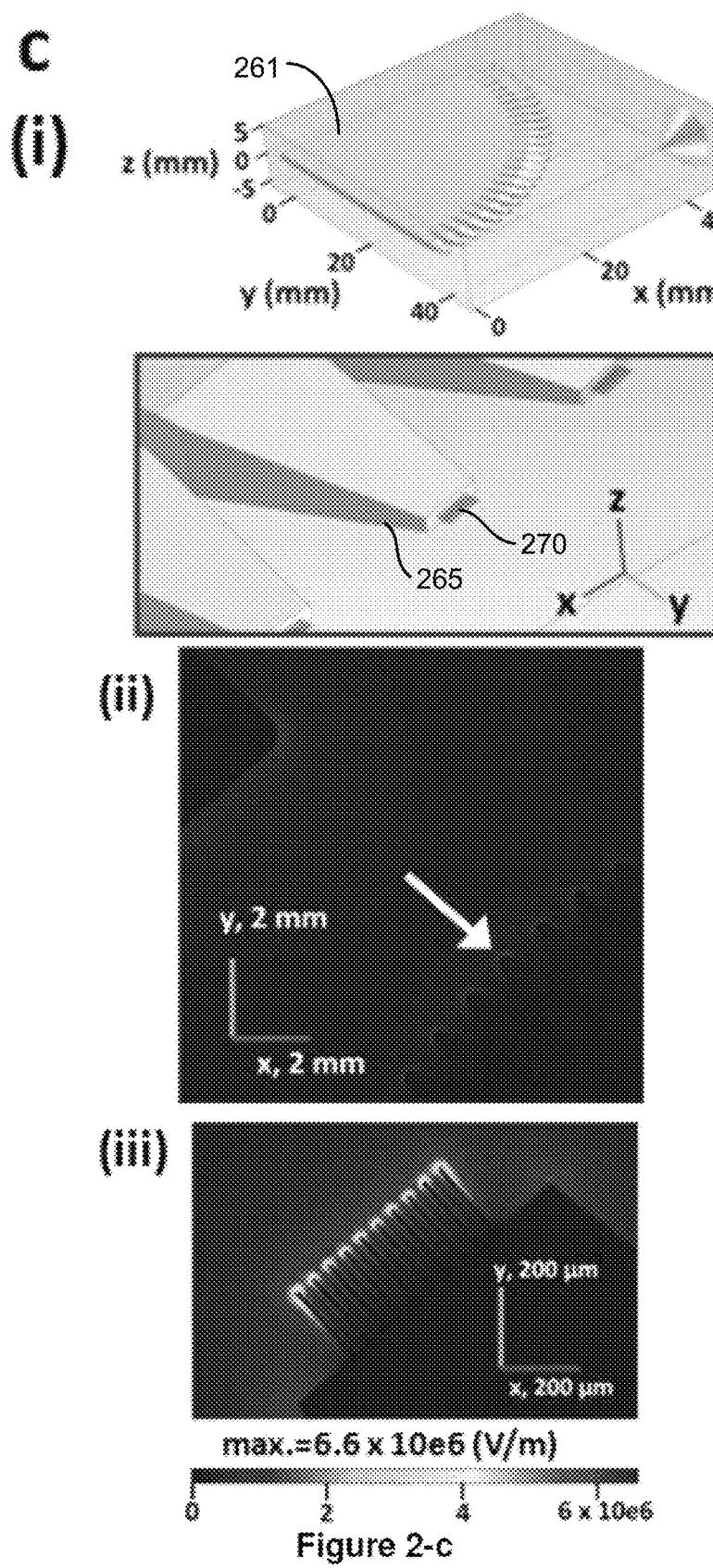
Figure 2-c

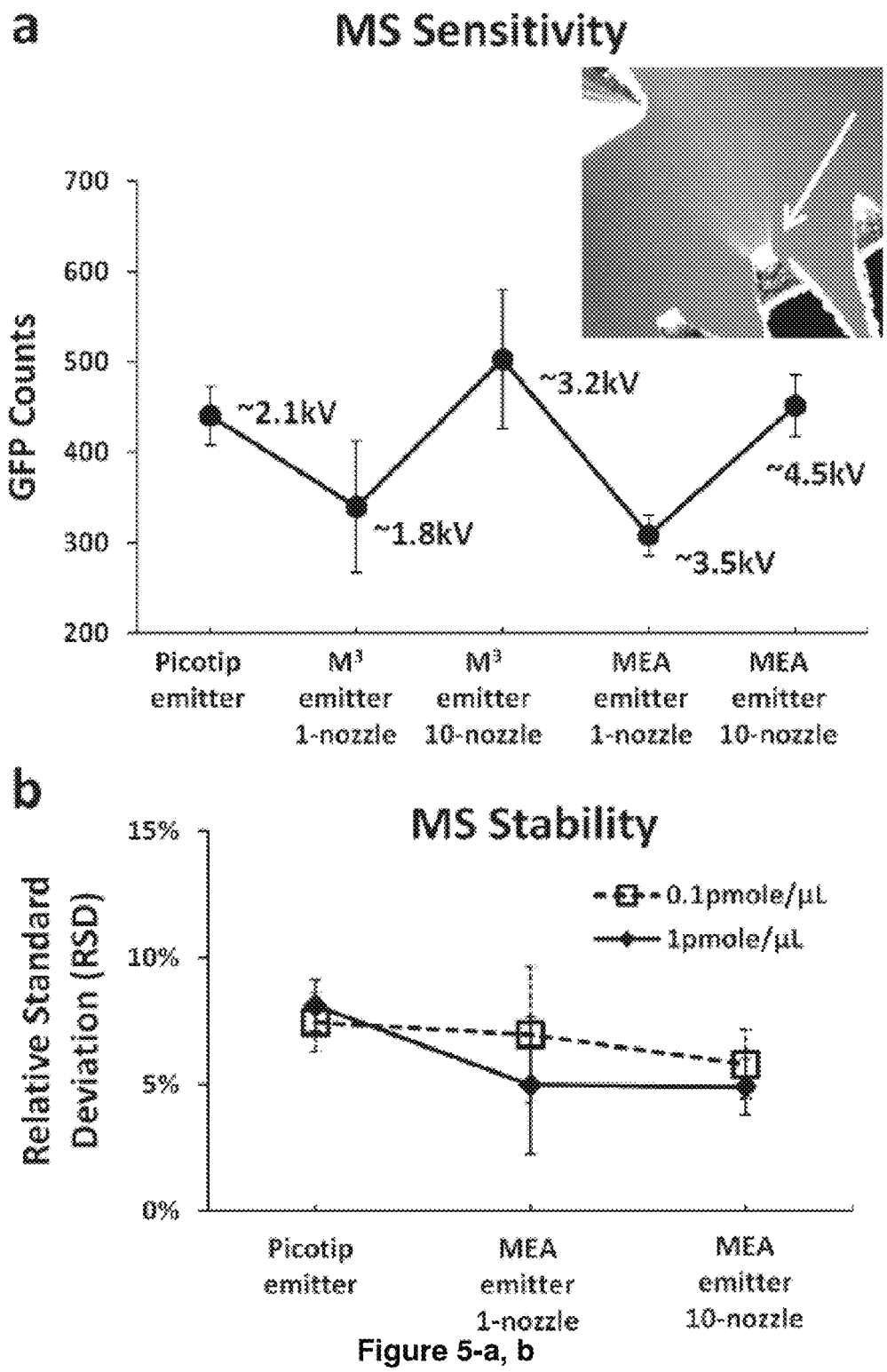
Figure 5-a, b

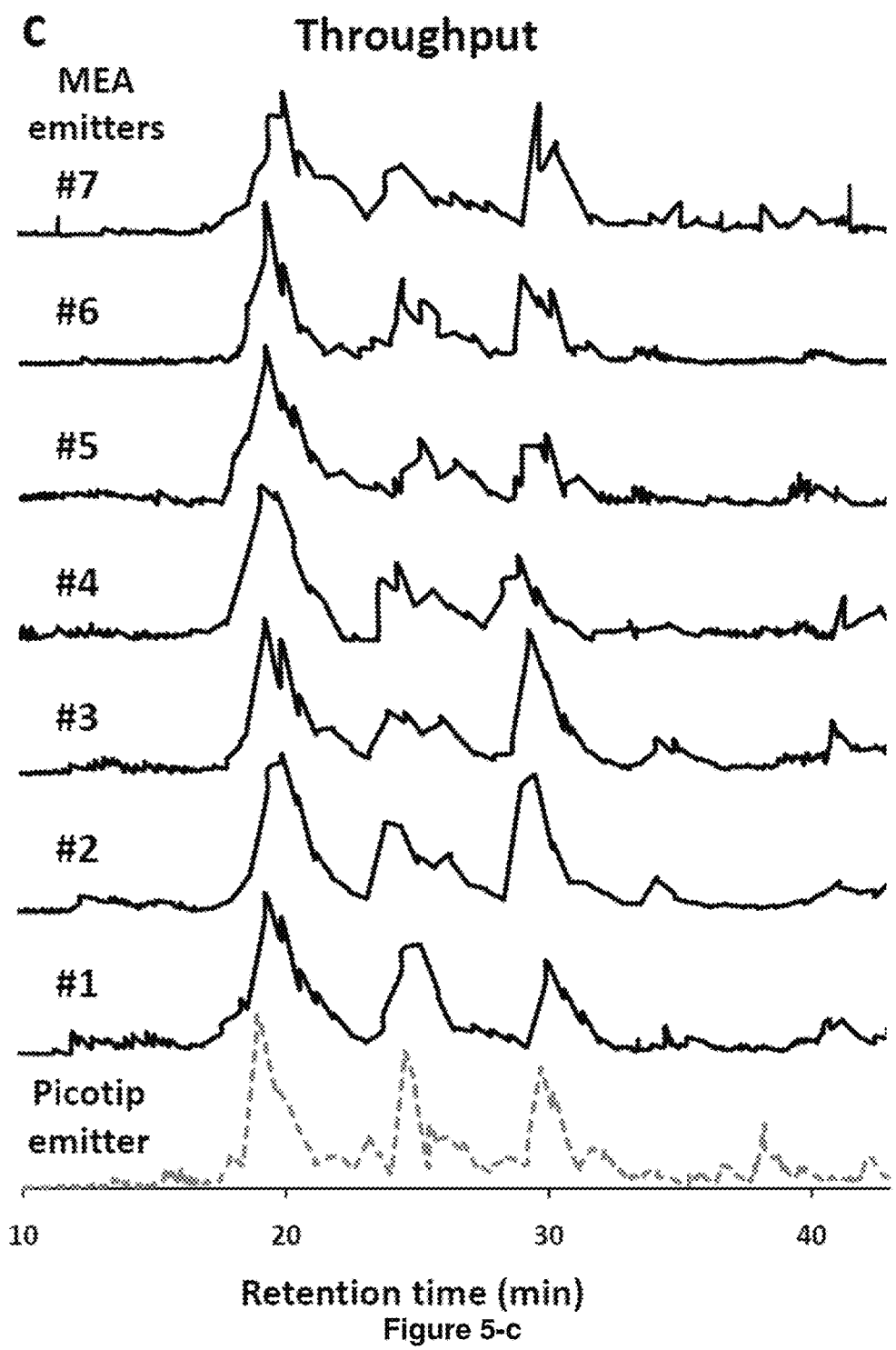
Figure 5-c a, Bare 4-inch silicon wafer, piranha cleaning
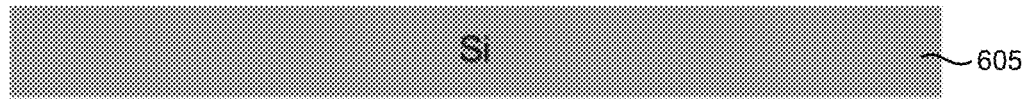
b, Photolithography to define channels/pillars and emitters
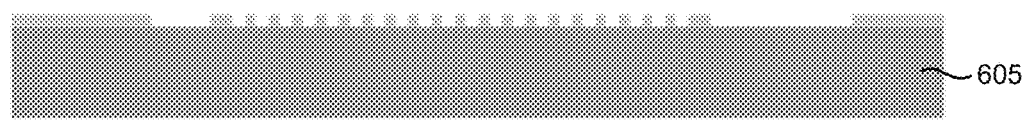
c, DRIE etching to create channels/pillars and emitters
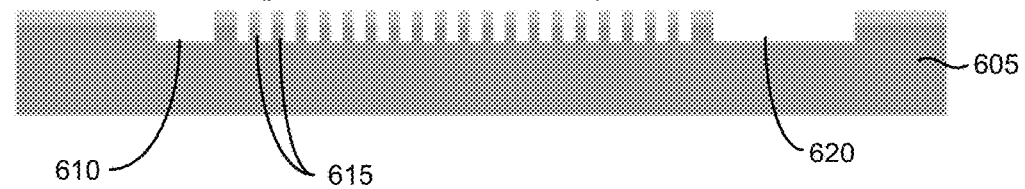
d, Photolithography and DRIE etching to create through-wafer access holes
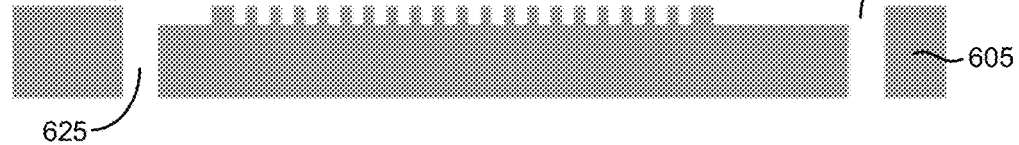
e, Thermal fusion wafer bonding
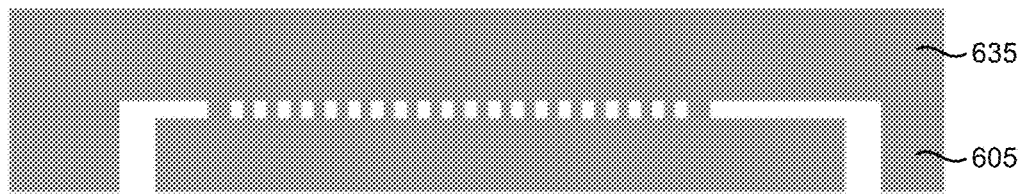
Figure 6

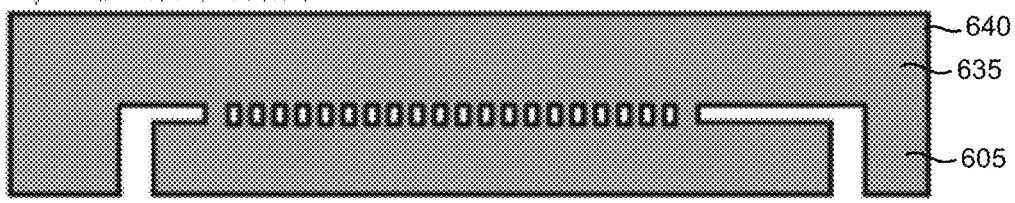
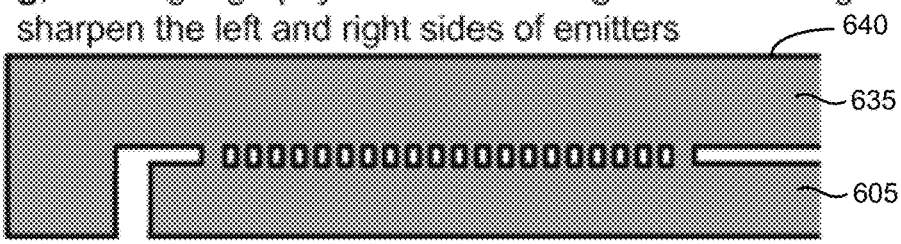
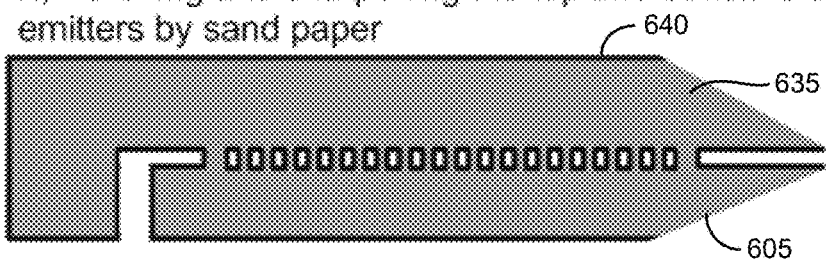
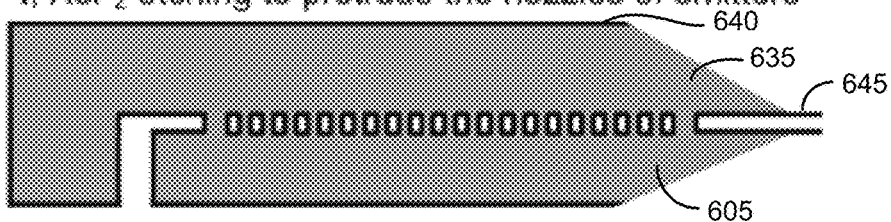
Figure 6

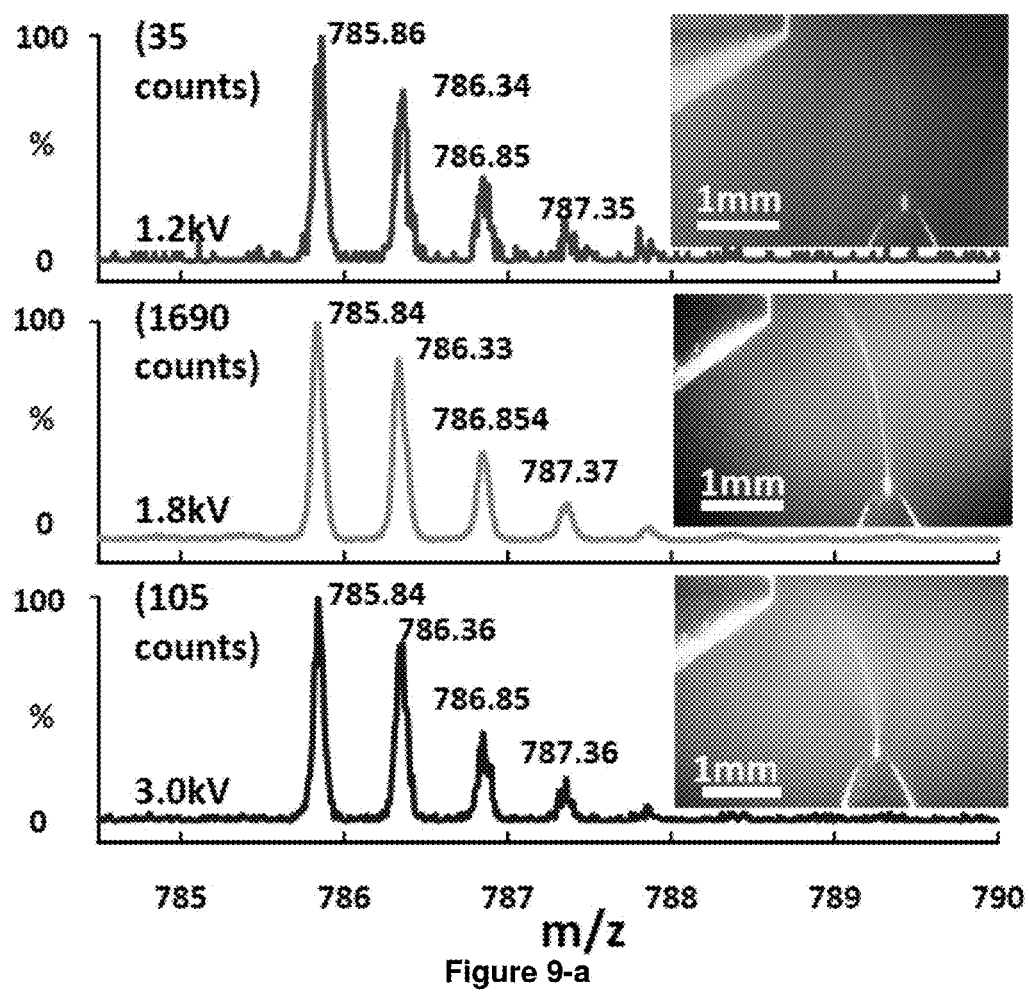
Figure 9-a

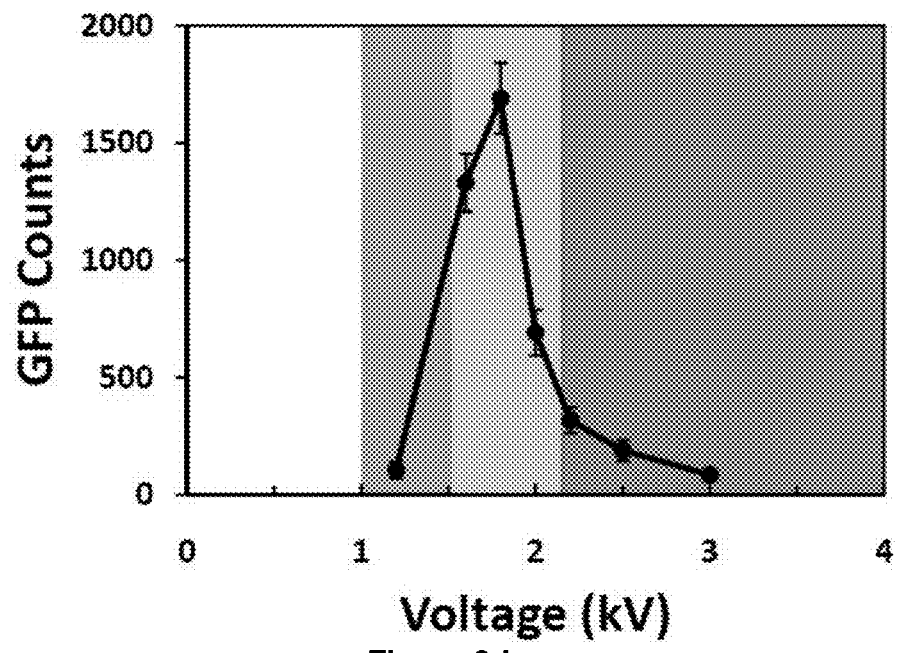
Figure 9-b
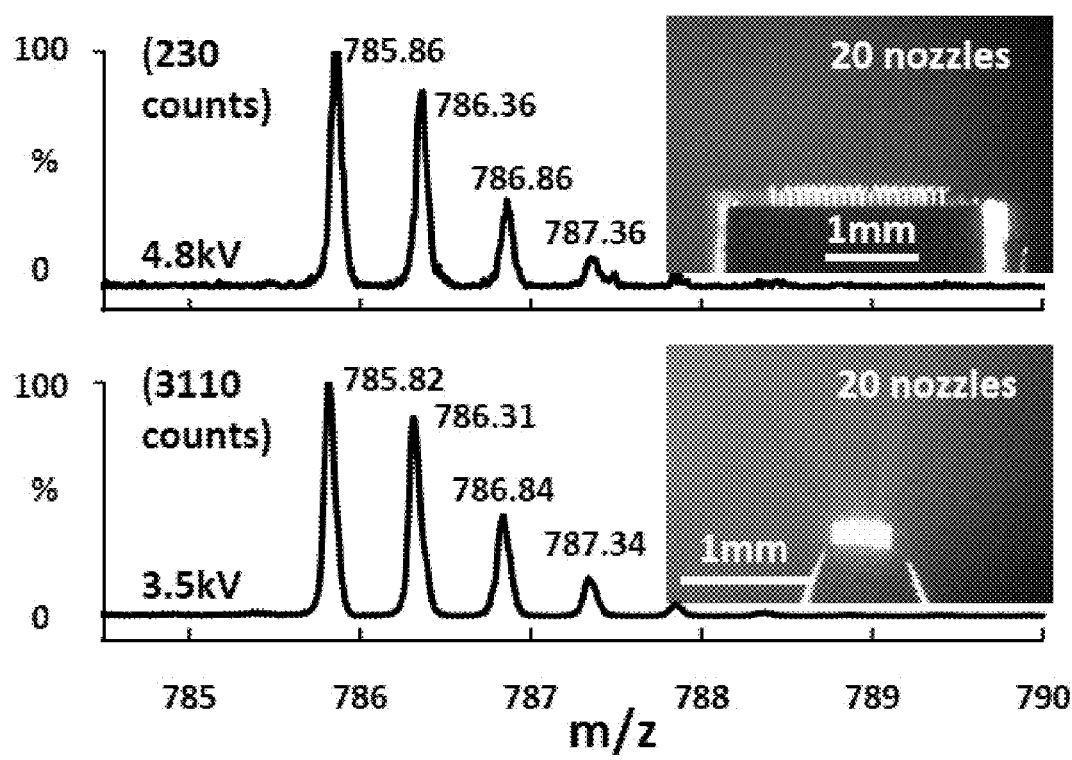
Figure 9-c

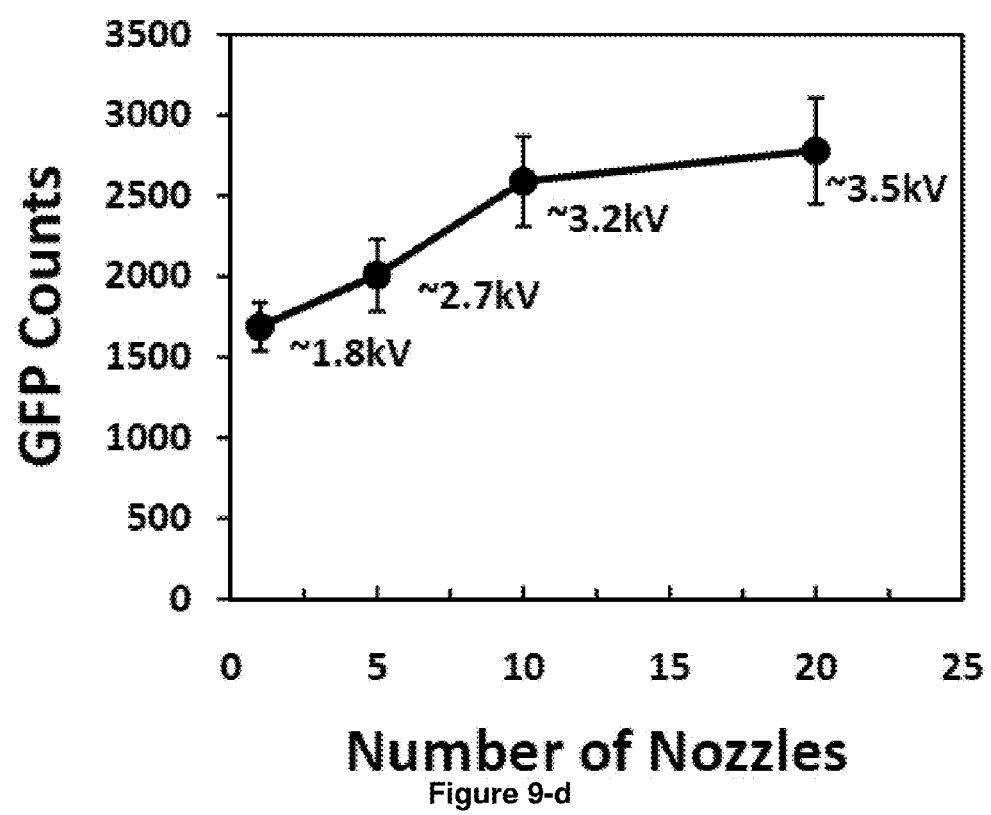
Figure 9-d

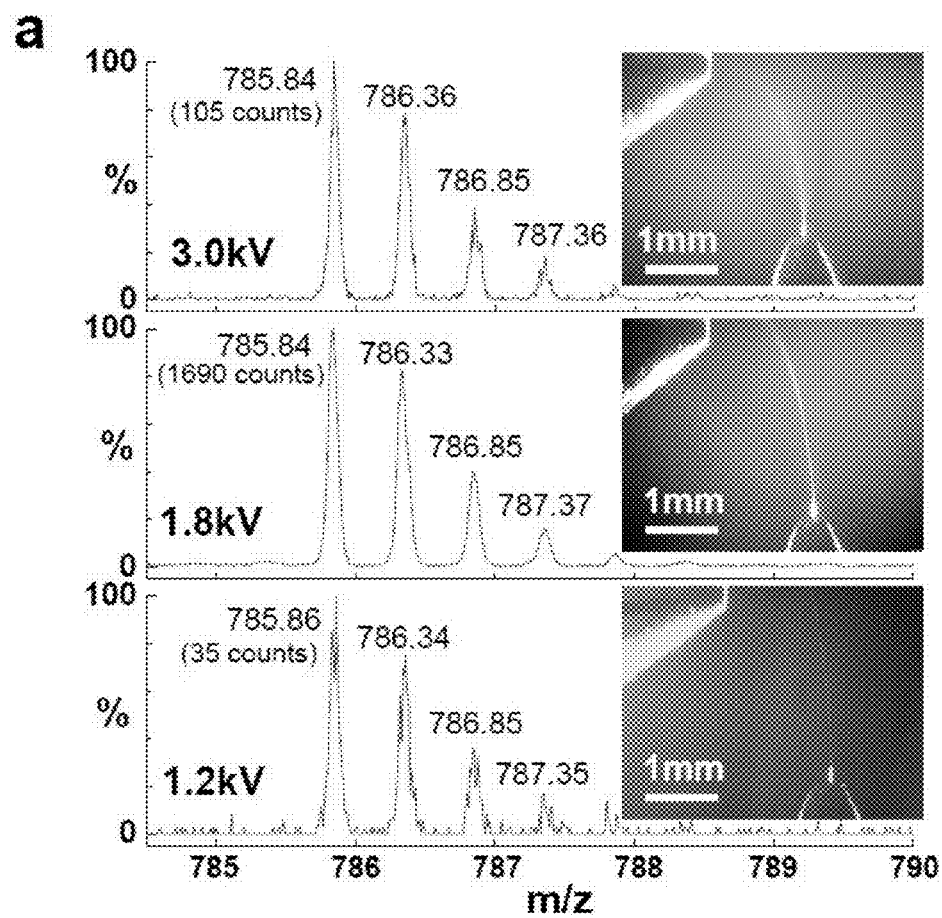
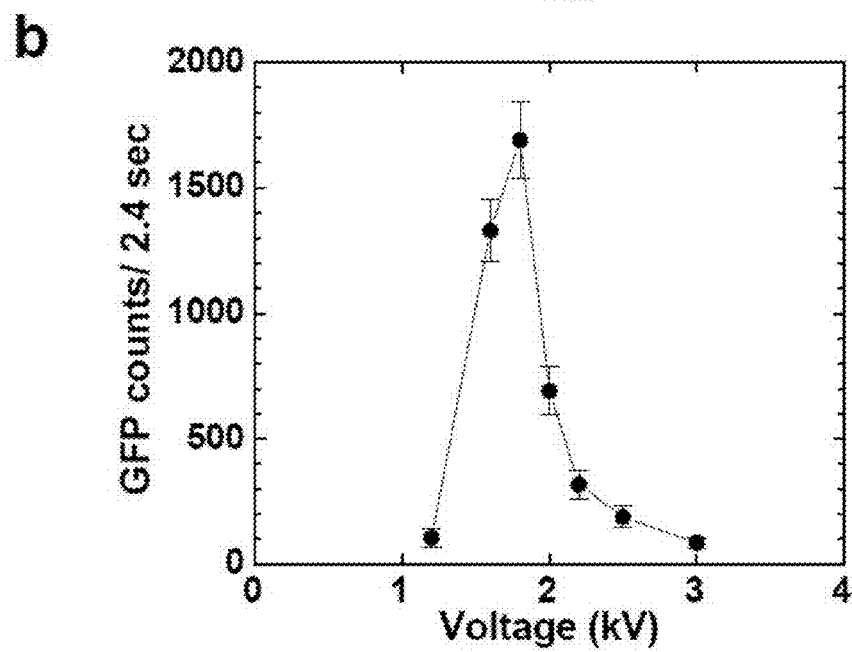
Figure 12

MULTINOZZLE EMITTER ARRAYS FOR ULTRAHIGH-THROUGHPUT NANOELECTROSPRAY MASS SPECTROMETRY

RELATED PATENT APPLICATIONS

The application claims priority as a continuation application of PCT International Patent Application No. PCT/US12/45082, filed Jun. 29, 2012, which claims priority to U.S. Provisional Patent Application Ser. No. 61/502,762, filed Jun. 29, 2011, which are herein incorporated by reference in their entireties.

STATEMENT OF GOVERNMENTAL SUPPORT

The invention was made with government support under Contract Nos. DE-AC02-05CH11231 awarded by the U.S. Department of Energy and Grant R21GM077870 awarded by the National Institutes of Health. The government has certain rights in the invention.

FIELD OF THE INVENTION

The present invention is in the field of electrospray ionization emitters and emitter arrays for mass spectrometry.

BACKGROUND OF THE INVENTION

Single Cell Omics unifies biology and technology and has become a new frontier. For mass spectrometry (MS)-based single cell proteomics and metabolomics, proof-of-principle experiments have been performed to characterize peptides and metabolites using matrix-assisted laser desorption ionization (MALDI)-MS and electrospray ionization (ESI)-MS. However, samples were processed individually offline and coverage of proteome and metabolome was limited in these studies. Key challenges still remain. First, further improvement in detection sensitivity; Second, extremely-efficient processing of minute amount of samples, down to a single cell; Third, high-throughput analysis in a cost-effective manner so that a large number of individual cells can be analyzed to achieve statistical significance. Since ESI-MS, particularly nano-ESI-MS, is the dominant soft ionization method for analyzing peptides and proteins, a fully-integrated microfluidic front-end system interfaced with nano-ESI-MS may serve as a unified platform to address the above-mentioned challenges. Microfluidics enables efficient sample manipulation and processing down to the picoliter even femtoliter range. Furthermore, the robustness and adaptability of microfabrication processes enables production of massively-parallel functional modules on a single chip for high-throughput analysis.

In fact, one of the actively-pursued areas in MS has been to implement the high-quality interface between microchips and mass spectrometers. Emitters based on polymeric materials, glass, and silicon using out-of-plane processes, had been fabricated. However, hydrophobic polymers have inherently undesirable properties for electrospray, such as a strong affinity to proteins and peptides and incompatibility with certain organic solvents; glass substrates are difficult to fabricate for complex structures; and out-of-plane strategy is critically limited in producing monolithically-integrated devices. Efforts in the field have led to two commercial MS-chips: Agilent's HPLC-chip made of polyimide and Waters' "nanoTile" chip made of ceramic. However, these devices have been developed for routine liquid chromatography (LC)-MS/MS applications and lack high-throughput capabilities. Their wide adoption by the research community remains to be seen because of their high costs and requirements for vendor-designated mass spectrometers.

Performing high-throughput ESI-MS remains a challenge because MS itself has a high capital and operational cost, limiting its scalability. Furthermore, MS is a serial detection system typically capable of analyzing one sample at a time. Hence, there is a tremendous demand in developing high-throughput MS front-end systems. One approach is to implement multiple LC systems in parallel that are coupled to a single MS detector. This reduces MS down time during sample injection and loading, and hence improves MS usage efficiency. Although in its infancy, the multiple-sprayer platform has been recognized as a potential high-quality interface for high-sensitivity and high-throughput ESI-MS. "Simultaneous multiple electrosprays" had been achieved with a bundle of fused silica capillaries and photonic fibers to improve MS sensitivity. However, the former has a size in the range of millimeters to centimeters and is not suitable for conventional mass spectrometers. Furthermore, neither of them is amenable for monolithic integration on a microchip. "Sequential multiple electrosprays" using multichannel, multitrack, out-of-plane multiple nozzles, and gated multi-inlets, had been implemented for high-throughput MS. In this approach, each sample is processed by a different front-end system (e.g., LC or CE) connected to an individual sprayer. This eliminates sample cross-contamination and allows efficient coupling between various components to reduce the dead volume/time. However, these devices also have intrinsic limitations in monolithic integration.

U.S. Patent Application Pub. No. 2010/0075428 discloses an electrospray emitter comprising: a first silica nozzle extending out from a larger silica base tube; wherein the walls of the nozzle and the base tube form a monolithic whole (hereby incorporated by reference).

SUMMARY OF THE INVENTION

The present invention provides for a structure comprising a plurality of emitters, wherein a first nozzle of a first emitter and a second nozzle of a second emitter emit in two directions that are not or essentially not in the same direction; wherein the walls of the nozzles and the emitters form a monolithic whole.

The present invention provides for an electrospray emitter comprising: a first nozzle and a second nozzle extending out from a larger base tube; wherein the walls of the nozzles and the base tube form a monolithic whole, wherein the first nozzle and the second nozzle emit in two directions that are not or essentially not in the same direction.

The present invention provides for a structure comprising: a base tube having a first end and a second end; and a plurality of smaller tubules, each tubule having a first end and a second end, the first ends of the tubules seamlessly connected to the second end of the base tube and the tubules extending out from the base tube; wherein the structure is monolithic and defines sealed, continuous fluid paths from the first end of the base tube to the second ends of the tubules, wherein at least the second end of a first tubule and the second end of a second tubule are oriented in two different or essentially different directions.

The present invention provides for a structure comprising an emitter with a sharpened end from which the emitter emits; wherein the emitters forms a monolithic whole.

The present invention provides for an electrospray emitter comprising: a first nozzle extending out from a larger base tube; wherein the walls of the nozzle and the base tube form a monolithic whole, wherein the nozzle has a sharpened end from which the nozzle emits.

The present invention provides for a structure comprising: a base tube having a first end and a second end; and a plurality of smaller tubules, each tubule having a first end and a second end, the first ends of the tubules seamlessly connected to the second end of the base tube and the tubules extending out from the base tube; wherein the structure is monolithic and defines sealed, continuous fluid paths from the first end of the base tube to the second ends of the tubules, wherein the second ends of the tubules are sharpened.

The present invention provides for a method for making a multinozzle emitter array comprising: (a) providing a first silicon substrate having a first surface, (b) etching a first trench into the first surface of the first substrate, (c) fusing a second silicon substrate onto the first surface of the first silicon substrate to form one or more channels, (d) oxidizing the exposed surfaces of the first and second silicon substrates to form a thermal oxidation layer over the exposed surfaces of the first and second silicon substrates, (e) cutting one or more ends of the first and second silicon substrates to form one or more nozzles from the one or more channels, optionally (f) sharpening the end of one or more nozzles, and optionally (g) etching the end of one or more sharpened nozzles to form an emitter nozzle that protrudes from the first and second silicon substrates.

The present invention provides for a method of improving sensitivity in mass spectrometry comprising integrating the electrospray nozzle of the present invention into the ion source of a mass spectrometer.

The present invention provides for a method of performing a variety of experiments on a protein sample, comprising integrating the electro spray nozzle of the present invention into a lab-on-a-chip.

The present invention provides for a method of studying ionization mechanisms in mass spectrometry comprising successively integrating each of a plurality of emitters of the present invention into an ion source of a mass spectrometer, each of the emitters having different inner cross section areas and different nozzle densities.

The present invention has one or more of the following advantages: The device minimize sample cross-contamination as each sample is analyzed by a separate individual emitter. The device improves reproducibility for parallel analysis because the emitters are highly reproducible and are identical or essentially identical to each other. Due the robustness and inert nature of the Si/SiO$_2$ material, the device can work under various conditions and can be reused many times by cleaning with harsh chemicals or heating to extreme temperatures. The throughput can be further improved by up-scaling the wafer size. The emitters can be seamlessly integrated with upstream complex components for biosample injection, separation and/or processing.

The present invention provides for a fully integrated separation of proteins and small molecules on a silicon chip before the electrospray mass spectrometry analysis, through either the monolithic column comprising of microfabricated micropillar arrays, or bead-packed columns, on chip.

The present invention provides for a method for making a multinozzle emitter array comprising: (a) performing photolithography and deep reactive ion etching (DRIE) to pattern and produce channels and emitters on a silicon wafer, (b) performing a second-layer photolithography and DRIE to define and create access holes with a second film mask, (c) performing thermal fusion bonding between the patterned wafer and another clean wafer, (d) wet oxidizing to grow a thick oxide of about 1 μm on all silicon surfaces including the sealed channels/emitters, (e) performing another photolithography and through-wafer etching steps to sharpen the left side and right side of the emitters, (f) releasing the chip from the wafer, (g) sharpening the top side and bottom side of the emitters by mechanically polishing the emitter stem with the sand paper, and (h) etching away silicon at the sharpened end of the emitters by selective XeF$_2$ etching.

The present invention provides for a method to implement a fully integrated separation of a mixture of proteins or small molecules on a silicon chip before electrospray mass spectrometry analysis, comprising: (a) providing the silicon chip comprising the structure or emitter of the present invention and one or more microfabricated micropillar arrays or bead-packed columns, (b) separating the proteins or small molecules of the mixture through one or more microfabricated micropillar arrays or bead-packed columns, (c) emitting the separated proteins or small molecules through the structure or emitter, and (d) analyzing the emitted separated proteins and/or small molecules by electrospray mass spectrometry analysis.

The present invention provides for a method for performing single cell analysis, comprising: (a) providing the structure or emitter of the present invention, and (b) performing a mass spectrometry-based single cell proteomics and/or metabolomics using the structure or emitter.

BRIEF DESCRIPTION OF THE DRAWINGS

The foregoing aspects and others will be readily appreciated by the skilled artisan from the following description of illustrative embodiments when read in conjunction with the accompanying drawings.

FIG. 2 shows simulated electric fields on MEA chips 201, 231, and 261. Three-dimensional electrostatic modeling for representative flat-end 205 (a), two-side sharpened-end 235 (b), and four-side sharpened-end 265 (c) emitters, is shown. Every emitter contains 10 nozzles (210, 240, and 270) each with a cross-section of 10 μm×10 μm. The 3D slice plots of electric fields on the three types of emitters (i), their relative position to the ion cone (ii), and the close-up views on the central emitters designated by the white arrows (iii), are shown. The voltage for the mass spectrometer ion cone and MEA chip is set to be 40 V and 3000 V, respectively. The maximum magnitude of the electric fields (V/m) at the nozzle tip of each type of emitters is highlighted on the scale bars individually (iii).

FIG. 5 shows high-throughput mass spectrometry using MEA emitters. (a) Comparison of MS sensitivity between different types of emitters. All GFP counts were obtained for 0.1 pmole/µL GFP in 50/50 acetonitrile/$H_2O$+0.1% formic acid with a flow rate of 0.6 µL/min. The optimal voltages to achieve the stable cone-jet mode spray are designated for each emitter. The insert shows a representative electrospray image for a 10-nozzle MEA emitter and its position relative to the ion cone (left). Error bars: s.d. (n≥10). (b) Comparison of stability between Picotips and MEA emitters for 0.1 and 1 pmole/µL GFP, respectively. Error bars: s.d. (n≥10). (c) Reproducibility of MEA emitters. The base peak intensity (BPI) chromatograms show HPLC gradient elution separation of 100 fmole tryptic digests of bovine serum albumin (BSA) with MS detection for 7 individual 10-nozzle MEA emitters and a Picotip emitter. The tested MEA emitters were randomly chosen from the 96 emitters on a MEA chip.

FIG. 6 shows schematics of the fabrication processes for MEA chips. (a) Cleaning of 4-inch silicon wafers 605 with a piranha solution. (b) Standard photolithography to define fluidic channels 610, micropillars 615, and emitters 620. (c) Deep reactive ion etching (DRIE) to create trenches with the desired depth. (d) Photolithography, followed by DRIE, to create through-wafer access holes 625 and 630. (e) Thermal fusion after cleaning of the wafer 605, contacting to another clean wafer 635, and annealing to form covalent Si—Si fusion bonding. (f) Growth of thermal oxide 640 on all surfaces. (g) Photolithography and through-wafer DRIE to sharpen the left and right sides of emitters and release the MEA chip from the wafer. (h) Polishing and sharpening of the top and bottom sides of emitters by the sand paper. (i) $XeF_2$ etching to protrude the nozzles 645.

FIG. 9 shows nanoelectrospray mass spectrometry with free-standing multinozzle emitters. (a) Voltage dependency of MS sensitivity for sharpened-end single-nozzle $M^3$ emitters. The mass spectra and GFP counts were obtained for 1 µM GFP B in 50/50 acetonitrile/$H_2O$+0.1% formic acid with a flow rate of 0.6 µL/min, and under three different voltages of 1.2 kV, 1.8 kV, and 3.0 kV, respectively. (b) Corresponding plot showing the dependence of GFP counts on applied voltages. Three different spray modes were observed and classified as pulsating (red), cone-jet (green), and multi-jet modes (blue). (c) Comparison of MS sensitivity between a flat-end and a four-side sharpened-end 20-nozzle $M^3$ emitter. Corresponding optical images of electrospray are shown in the inserts. (d) Dependence of MS sensitivity on the number of nozzles for sharpened-end $M^3$ emitters. The optimal voltages to achieve the stable cone-jet mode spray are designated for each corresponding number of nozzles. All nozzles have a cross-section of 10 µm×10 µm. Standard deviation (s.d.) was calculated for a 10-minute scan under indicated optimal voltages. Error bar: s.d. (n≥10).

FIG. 12 shows voltage-dependent mass spectrometry sensitivity of sharpened single-nozzle emitter. (a) mass spectra of 1 µM GFP B obtained from a sharpened single-nozzle emitter biased at 1.2 kV, 1.8 kV, and 3.0 kV, respectively. The inserts show corresponding optical images of electrospray (center) relative to the sample cone (upper left). (b) dependence of total ion counts of 1 µM GFP B (m/z=785.8) on voltages applied at the emitters. Standard deviation was calculated for a 10-minute scan under each voltage. Scale bar shows 1 mm.

DETAILED DESCRIPTION OF THE INVENTION

Figure 1:
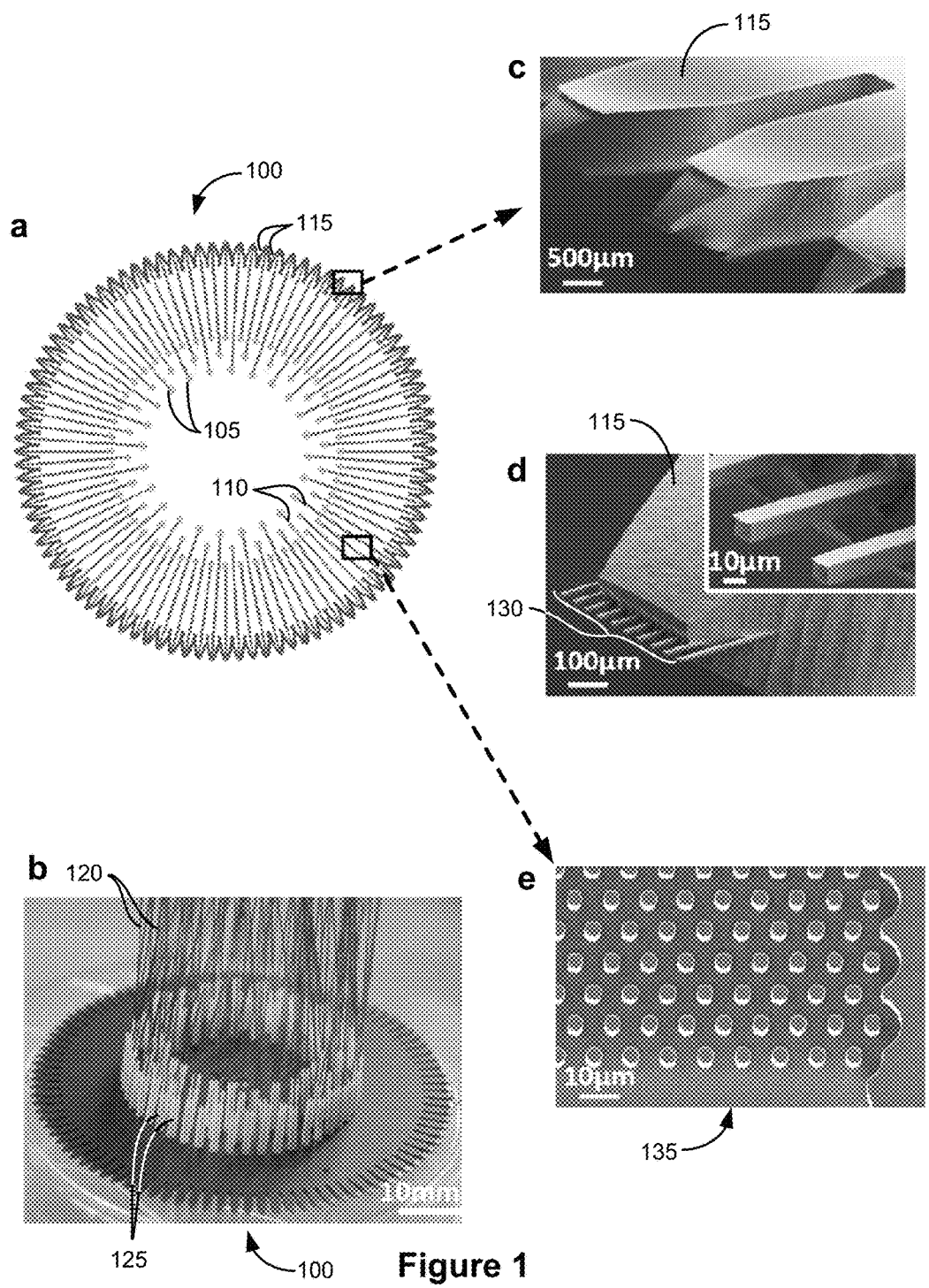
FIG. 1 shows a multinozzle emitter array chip. (a) A plan view of a 96-emitter array chip 100. The circles 105 represent through-holes for sample injection. The lines 110 represent microfluidic channels of 400 μm in width and 10 μm in depth, which can be embedded with ordered micropillar arrays. The curves 115 represent the sharpened features of the multinozzle emitters. (b) High-definition photograph of a 3-inch MEA chip 100 fabricated from 4-inch silicon wafers. The device is connected to 96 silica capillaries 120 via the PTFE tubing 125. (c), (d) SEM images of 10-nozzle emitters 115 with different magnifications. Each emitter 115 consists of a linear 10-nozzle array 130, with a conduit length of around 100 μm and a cross-section of 10 μm×10 μm, protruding out from a hollow silicon sliver. The internozzle spacing is 40 μm. (e) SEM images of micropillar-arrays 135 within a main channel. The pillars are 10 μm deep with a diameter of 4.5 μm and spaced by 5.5 μm. They are arranged according to an equilateral triangular grid. Boxes in (a) indicate the corresponding zoom-in regions for (c) and (e), respectively.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to "nozzle" includes a single nozzle as well as a plurality of nozzles, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "nozzle," "capillary," and "tubule" are used interchangeably in this disclosure to mean a very thin tube out of which an analyte solution can flow and form small droplets. The term "emitter" is used to mean the assembly that includes both the nozzle(s) and a base chamber or tube that supplies an analyte solution to the nozzle(s). In the case of a single nozzle, the terms "emitter" and "nozzle" can refer to the same structure as there is a one-to-one correspondence between the nozzle and its base chamber; the base chamber can be thought of as a simple extension of the nozzle. The term "trench" is used to mean a groove or ditch in a surface. The term "channel" is used to mean a trench that has been enclosed to form a hollow elongated structure, such as a cylinder. A channel can have a circular, square, rectangular, triangular, or any polygonal or closed curve cross section. The term "monolithic" is used to mean consisting of one piece, solid and unbroken. In a monolithic structure there are no joints or seams. The terms nanospray and nanoelectrospray are used interchangeably to mean electrospray at nanoliter/min flow rates. The term "femtoelectrospray" is used to describe electrospray at femtoliter/min flow rate.

The embodiments of the invention are illustrated in the context of nanoelectrospray emitters for mass spectrometry. The skilled artisan will readily appreciate, however, that the materials and methods disclosed herein will have application in a number of other contexts where very small droplet size and very slow fluid flow rates are desirable.

Electrospray ionization (ESI) is a technique used in mass spectrometry to produce ions using a nozzle, capillary, or tubule. ESI is especially useful in producing ions from macromolecules because it overcomes the propensity of these molecules to fragment when ionized. One important variation on the basic electrospray technique, which generally offers better sensitivity, is nanospray ionization, in which the flow rate of the analyte solution is microliters/minute (μL/min) or nanoliters/minute (nL/min).

Silica ($SiO_2$) nanotubes can be especially useful as ESI emitters because of their ease of formation and possibilities for surface functionalization. In addition, their hydrophilic properties make silica electrospray emitters intrinsically more compatible with a wide variety of biomolecules than electrospray emitters made from hydrophobic polymers. Studies in nanofluidics have shown that biomolecules can indeed be transported through hydrophilic silica nanotubes.

In some embodiments of the invention, the structure, emitter, and nozzle comprise Si and/or $SiO_2$ (silica). In some embodiments of the invention, the structure and emitter are fabricated from a silicon substrate, such as a silicon wafer. In some embodiments of the invention, the silicon wafer can be any size, such as a four-inch, six-inch or eight-inch silicon wafer. The same strategy can be applied to glass substrates.

In some embodiments of the invention, the emitter comprises a base tube or base channel in fluid communication with the nozzles, wherein the walls of the nozzles and the base channel form a monolithic whole. In some embodiments of the invention, the base channel is a base tube or a microfluidic channel.

In some embodiments of the invention, the first nozzle and/or the second nozzle are sharpened. In some embodiments of the invention, all of the nozzles of the emitter are sharpened.

In some embodiments of the invention, the nozzle is a nanotube. A plurality of the nozzles can form a nanotube array.

In some embodiments of the invention, a first emitter is oriented such that the first emitter points in a direction directly or essentially opposite to the direction pointed by a second emitter. In some embodiments of the invention, the emitters are oriented such that the emitters point out in radial configuration.

In some embodiments of the invention, the end of an emitter can comprise a flat-end, two-side sharpened-end, or four-side sharpened-end.

In some embodiments of the invention, each structure comprises equal to or more than about 10 emitters. In some embodiments of the invention, each structure comprises equal to or more than about 20 emitters. In some embodiments of the invention, each structure comprises equal to or more than about 30 emitters. In some embodiments of the invention, each structure comprises equal to or more than about 40 emitters. In some embodiments of the invention, each structure comprises equal to or more than about 50 emitters. In some embodiments of the invention, each structure comprises equal to or more than about 90 emitters. In some embodiments of the invention, each structure comprises equal to or more than about 100 emitters.

In some embodiments of the invention, each emitter comprises equal to or more than about 10 nozzles. In some embodiments of the invention, each emitter comprises equal to or more than about 20 nozzles. In some embodiments of the invention, each emitter comprises equal to or more than about 30 nozzles. In some embodiments of the invention, each emitter comprises equal to or more than about 40 nozzles. In some embodiments of the invention, each emitter comprises equal to or more than about 50 nozzles. In some embodiments of the invention, each emitter comprises equal to or more than about 100 nozzles.

Each nozzle has a first end seamlessly connected with the emitter, and a second end comprises an aperture or opening. In some embodiments of the invention, the aperture or opening of each nozzle has a cross-section that is a square or essentially square shape. In some embodiments of the invention, the length of each side of the square or essentially square shape is equal to or less than about 20 µm, 15 µm, 10 µm, 5 µm, 3 µm, 2 µm, or 1 µm.

In some embodiments of the invention, the aperture or opening of each nozzle has a cross-section that is a circular or essentially circular shape. In some embodiments of the invention, the diameter of the circular or essentially circular shape is equal to or less than about 20 µm, 15 µm, 10 µm, 5 µm, 3 µm, 2 µm, or 1 µm. The cross-section of the aperture or opening of the nozzles can be square, rectangular, circular, or triangular in shape.

In some embodiments of the invention, the aperture or opening of each nozzle has a cross-section with a longest linear dimension equal to or less than about 20 µm, 15 µm, 10 µm, 5 µm, 3 µm, 2 µm, or 1 µm.

In some embodiments of the invention, the emitter is a one- to 40-nozzle emitter wherein each nozzle comprises a cross-section of about 2 µm to about 10 µm×about 2 µm to about 10 µm. In some embodiments of the invention, the emitter is a one-nozzle emitter wherein the nozzle comprises a cross-section of about 10 µm×about 10 µm. In some embodiments of the invention, the emitter is a 20-nozzle emitter wherein each nozzle comprises a cross-section of about 5 µm×about 5 µm. In some embodiments of the invention, the emitter is a 40-nozzle emitter wherein each nozzle comprises a cross-section of about 2 µm×about 2.5 µm.

In some embodiments of the invention, the emitter is a sharpened-end multinozzle emitters.

The present invention also provides for a silicon chip comprising the structure or emitter of the present invention.

In some embodiments of the invention, the chip, structure or emitter of the present invention is suitable for high-sensitivity and high-throughput mass spectrometry. In some embodiments of the invention, the chip, structure or emitter of the present invention are suitable for single cell analysis. In some embodiments of the invention, the chip, structure or emitter of the present invention are suitable for single cell analysis in an ultrahigh-throughput manner.

Each of the emitter or nozzle is in fluid communication with a base tube or channel. In some embodiments of the invention, the base tube or channel is a microfluidic channel. In some embodiments of the invention, the chip, structure or emitter can further comprise a through-hole which is in fluid communication with the base tube or channel. In some embodiments of the invention, the through-hole is at an angle, such as perpendicular, relative to the base tube or channel. In some embodiments of the invention, the chip, structure or emitter further comprises a tubing in fluid communication to each through-hole. The tubing can comprise a flexible or rigid material. The tubing can comprise a polymer, such as polytetrafluoroethylene (PTFE).

In some embodiments of the invention, the structure comprises a multinozzle emitter array (MEA) chip. In some embodiments of the invention, the structure comprises a 96-emitter array chip. Each emitter is in fluid communication with a through-hole of the chip for sample injection. Each through-hole is in fluid communication with a microfluidic channel of about 400 µm in width and 10 µm in depth, which can be embedded with ordered micropillar arrays. The micronozzle emitters comprise sharpened features. The structure can be a 3-inch MEA chip fabricated from a 4-inch silicon wafer. The structure can be further connected to 96 silica capillaries via PTFE tubing.

In some embodiments of the invention, the structure comprises one or more emitter, wherein each emitter comprises about 10-nozzles. Each nozzle comprises a conduit length of around 100 µm and a cross-section of about 10 µm×about 10 µm, protruding out from a hollow silicon sliver. The inter-nozzle spacing can be about 40 µm.

In some embodiments of the invention, the structure comprises a micropillar-array within a main channel. The pillars can be about 10 µm deep with a diameter of about 4.5 µm and spaced by about 5.5 µm. They can be arranged according to an equilateral triangular grid. The parameters of the micropillar array, including but not limited to the diameter and shape of the pillars and interpillar spacing, can be varied. In addition, instead of having a micropillar array, a main channel can be packed with functional beads for bioseparation, such as 5 µm C18 beads.

In some embodiments of the invention, the structure is a MEA chip provided in a mass spectrometer ion cone and the MEA chip is set to be 40 V and 3000 V, respectively. In some embodiments of the invention, the maximum magnitude of an electric field (V/m) at the nozzle tip of an emitter ranges from about 2.0 to about 5.0 kV. In some embodiments of the invention, the maximum magnitude of an electric field (V/m) at the nozzle tip of an emitter ranges from about 2.3 to about 4.5 kV. In one embodiment of the invention, the maximum magnitude of an electric field (V/m) at the nozzle tip of a four-side sharpened-end 1-nozzle MEA emitter, wherein the nozzle has a cross-section of about 10 µm×about 10 µm, ranges from about 2.3 to about 3.3 kV. In one embodiment of the invention, the maximum magnitude of an electric field (V/m) at the nozzle tip of a four-side sharpened-end 10-nozzle MEA emitter, wherein each nozzle has a cross-section of about 10 µm×about 10 µm, ranges from about 3.0 to about 4.5 kV.

In some embodiments of the invention, the emitter is capable of a total flow rate of from more than 0 µL/min to about 6.0 µL/min. In some embodiments of the invention, the emitter is capable of a total flow rate of from about 0.2 µL/min to about 6.0 µL/min. In some embodiments of the invention, the emitter is capable of a total flow rate of equal to or more than 1.4 µL/min. In some embodiments of the invention, the emitter is capable of a total flow rate of equal to or more than 6.0 µL/min. In some embodiments of the invention, the emitter is capable of a total flow rate of about 0.6 µL/min.

In some embodiments of the invention, the method of the present invention further comprises the step of cleaning, such as piranha cleaning, the first surface of the first silicon substrate prior to the (b) etching step. In some embodiments of the invention, the (b) etching step comprises using photolithography to define the areas on the first surface of the first substrate where the trench is to be etched. In some embodiments of the invention, the (b) etching step comprises deep reactive ion etching (DRIE). In some embodiments of the invention, the method further comprises a second etching step subsequent to the (b) etching step to form channels through the first silicon substrate, such as through wafer access holes. In some embodiments of the invention, the method further comprises a second etching step comprises using photolithography to define the areas on the first surface of the first substrate where the channels through the first silicon substrate is to be etched. In some embodiments of the invention, the second etching step comprises deep reactive ion etching (DRIE). In some embodiments of the invention, the (e) cutting step comprises DRIE. In some embodiments of the invention, the (f) sharpening step comprises using a sand paper to sharpen and/or polish the end of the one or more sharpened nozzles. In some embodiments of the invention, the (g) etching step comprises using $XeF_2$ etching.

In some embodiments of the invention, the method comprises performing photolithography and deep reactive ion etching (DRIE) to pattern and produce channels (with micropillar arrays if needed) and emitters on a 4-inch silicon wafer, performing a second-layer photolithography and DRIE to define and create access holes with a second film mask, performing thermal fusion bonding between the patterned wafer and another clean wafer, wet oxidizing to grow a thick oxide of about 1 μm on all silicon surfaces including the sealed channels/emitters, performing another photolithography and through-wafer etching steps to sharpen the emitters (left and right), releasing the chip from the wafer, sharpening the other two sides (top and bottom) of the emitters by mechanically polishing the emitter stem with the sand paper, and etching away silicon at the sharpened end of the emitters by selective $XeF_2$ etching. This method produces an emitter comprising one or more protruding nozzles made of $SiO_2$.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Multinozzle Emitter Arrays for Nanoelectrospray Mass Spectrometry

Mass spectrometry (MS) is the enabling technology for proteomics and metabolomics. However, dramatic improvements in both sensitivity and throughput are still required to achieve routine MS-based single cell proteomics and metabolomics. Here, we report the silicon-based monolithic multinozzle emitter array (MEA), and demonstrate its proof-of-principle applications in high-sensitivity and high-throughput nanoelectrospray mass spectrometry. Our MEA consists of 96 identical 10-nozzle emitters in a circular array on a 3-inch silicon chip. The geometry and configuration of the emitters, the dimension and number of the nozzles, and the micropillar arrays embedded in the main channel, can be systematically and precisely controlled during the microfabrication process. Combining electrostatic simulation and experimental testing, we demonstrated that sharpened-end geometry at the stem of the individual multinozzle emitter significantly enhanced the electric fields at its protruding nozzle tips, enabling sequential nanoelectrospray for the high-density emitter array. We showed that electrospray current of the multinozzle emitter at a given total flow rate was approximately proportional to the square root of the number of its spraying-nozzles, suggesting the capability of high MS sensitivity for multinozzle emitters. Using a conventional Z-spray mass spectrometer, we demonstrated reproducible MS detection of peptides and proteins for serial MEA emitters, achieving sensitivity and stability comparable to the commercial capillary emitters. Our robust silicon-based MEA chip opens up the possibility of a fully-integrated microfluidic system for ultrahigh-sensitivity and ultrahigh-throughput proteomics and metabolomics.

Single Cell Omics unifies biology and technology and has become a new frontier.[1] For mass spectrometry (MS)-based single cell proteomics and metabolomics, proof-of-principle experiments have been performed to characterize peptides and metabolites using matrix-assisted laser desorption ionization (MALDI)-MS[2-4] and electrospray ionization (ESI)-MS.[5,6] However, samples were processed individually offline and coverage of proteome and metabolome was limited in these studies. Key challenges still remain. First, further improvement in detection sensitivity; Second, extremely-efficient processing of minute amount of samples, down to a single cell; Third, high-throughput analysis in a cost-effective manner so that a large number of individual cells can be analyzed to achieve statistical significance. Since ESI-MS,[7] particularly nano-ESI-MS,[8] is the dominant soft ionization method for analyzing peptides and proteins, a fully-integrated microfluidic front-end system interfaced with nano-ESI-MS may serve as a unified platform to address the above-mentioned challenges. Microfluidics enables efficient sample manipulation and processing down to the picoliter even femtoliter range.[9] Furthermore, the robustness and adaptability of microfabrication processes enables production of massively-parallel functional modules on a single chip for high-throughput analysis.

In fact, one of the actively-pursued areas in MS has been to implement the high-quality interface between microchips and mass spectrometers.[10] Emitters based on polymeric materials,[11-15] glass,[16,17] and silicon using out-of-plane processes,[18] had been fabricated. However, hydrophobic polymers have inherently undesirable properties for electrospray, such as a strong affinity to proteins and peptides and incompatibility with certain organic solvents; glass substrates are difficult to fabricate for complex structures; and out-of-plane strategy is critically limited in producing monolithically-integrated devices. Efforts in the field have led to two commercial MS-chips: Agilent's HPLC-chip made of polyimide and Waters' "nanoTile" chip made of ceramic. However, these devices have been developed for routine liquid chromatography (LC)-MS/MS applications and lack high-throughput capabilities. Their wide adoption by the research community remains to be seen because of their high costs and requirements for vendor-designated mass spectrometers.

Performing high-throughput ESI-MS remains a challenge because MS itself has a high capital and operational cost, limiting its scalability. Furthermore, MS is a serial detection system typically capable of analyzing one sample at a time. Hence, there is a tremendous demand in developing high-throughput MS front-end systems. One approach is to implement multiple LC systems in parallel that are coupled to a single MS detector. This reduces MS down time during sample injection and loading, and hence improves MS usage efficiency. Although in its infancy, the multiple-sprayer platform has been recognized as a potential high-quality interface for high-sensitivity and high-throughput ESI-MS.[19] "Simultaneous multiple electrosprays" had been achieved with a bundle of fused silica capillaries[20] and photonic fibers[21] to improve MS sensitivity. However, the former has a size in the range of millimeters to centimeters and is not suitable for conventional mass spectrometers. Furthermore, neither of them is amenable for monolithic integration on a microchip. "Sequential multiple electrosprays" using multichannel,[22, 23] multitrack,[24] out-of-plane multiple nozzles,[18] and gated multi-inlets,[25] had been implemented for high-throughput MS. In this approach, each sample is processed by a different front-end system (e.g., LC or CE) connected to an individual sprayer. This eliminates sample cross-contamination and allows efficient coupling between various components to reduce the dead volume/time. However, these devices also have intrinsic limitations in monolithic integration.

We had previously developed microfabricated monolithic multinozzle emitters ($M^3$ emitters) for nanoelectrospray mass spectrometry.[26] Our in-plane strategy allows ease and flexibility in design, integration, and interfacing to MS. However, the high operating voltage (≥4.5 kV) required even for the low-nozzle-number $M^3$ emitters (up to 5 nozzles) to achieve stable electrospray remained problematic. This prevented us from implementing high-nozzle-number $M^3$ emitters (>10 nozzles). Herein, we report a novel approach to create monolithic multinozzle emitter arrays (MEAs) for nanoelectrospray mass spectrometry. We demonstrate two key technical breakthroughs in these devices. First, high-density (up to 96) emitters were constructed in a circular array format on a 3-inch silicon chip (i.e., MEA chip), utilizing the concept of "sequential multiple electrosprays" and hence enabling high-throughput applications. Second, sharpened-end emitters with a large number of nozzles (up to 40) per emitter were engineered on the MEA chip, utilizing the concept of "simultaneous multiple electrosprays" and hence enabling high-sensitivity MS detections. We further demonstrate the applicability of our MEA chips for metabolomics and proteomics applications via MS analyses of peptides and tryptic digests.

Experimental Section

Design and Fabrication of MEA Chips

MEA chips were designed using the L-Edit software (v15, Tanner Research Inc.). The procedures to fabricate the MEA chips were improved from those for $M^3$ emitters[26] and involved 9 major steps (FIG. 6a-i). First, we performed standard photolithography and deep reactive ion etching (DRIE) to pattern and produce channels 610 (with micropillar arrays 615 if needed) and emitters 620 on a 4-inch silicon wafer 605 (a-c). Then, we performed second-layer photolithography and DRIE to define and create access holes 625 and 630 with a second film mask (d). Next, we performed thermal fusion bonding between the patterned wafer 605 and another clean wafer 635 (e), followed by wet oxidation to grow a thick oxide 640 of ~1 μm on all silicon surfaces including the sealed channels/emitters (f). Afterwards, we performed another photolithography and through-wafer etching steps to sharpen the emitters (left- and right-side, FIG. 1 and FIG. 2) and release the chip from the wafer (g). Subsequently, we sharpened the other two sides (top and bottom, FIG. 1 and FIG. 2) of the emitters by mechanically polishing the emitter stem with the sand paper (h). Finally, we etched away silicon at the sharpened end of the emitters by selective $XeF_2$ etching (i). This final step ended up with protruding nozzles 645 made of $SiO_2$. The fabricated devices were examined by optical microscopy using a Reichert-Jung Polylite 88 microscope (Reichert Microscope Services), and by scanning electron microscopy using a JEOL 6340F FEG-SEM (JEOL Ltd.).

Electrostatic Simulations of MEA Emitters

The multiphysics modeling and simulation software COMSOL (v4.1, COMSOL Inc.) was used to simulate electric fields of 10-nozzle MEA emitters with flat-end, two-side sharpened-end, and four-side sharpened-end features. For simplicity, we did not take into account the presence of complex dynamic gas/fluid behaviors during the actual electrospray process, and only considered static electric fields on MEA emitters relative to the Z-spray sample cone of the Q-TOF API US mass spectrometer (Waters Corp.). Furthermore, we simulated a quadrant instead of the whole device to reduce the dimensions of modeling. The 3D geometry was constructed with the parameters similar to the actual experimental setup. Calculated electric fields were analyzed by 3D slice plots on the central plane (z=0). The detailed simulation parameters are provided herein.

Electrospray Current Measurement of MEA Emitters

Figure 8:
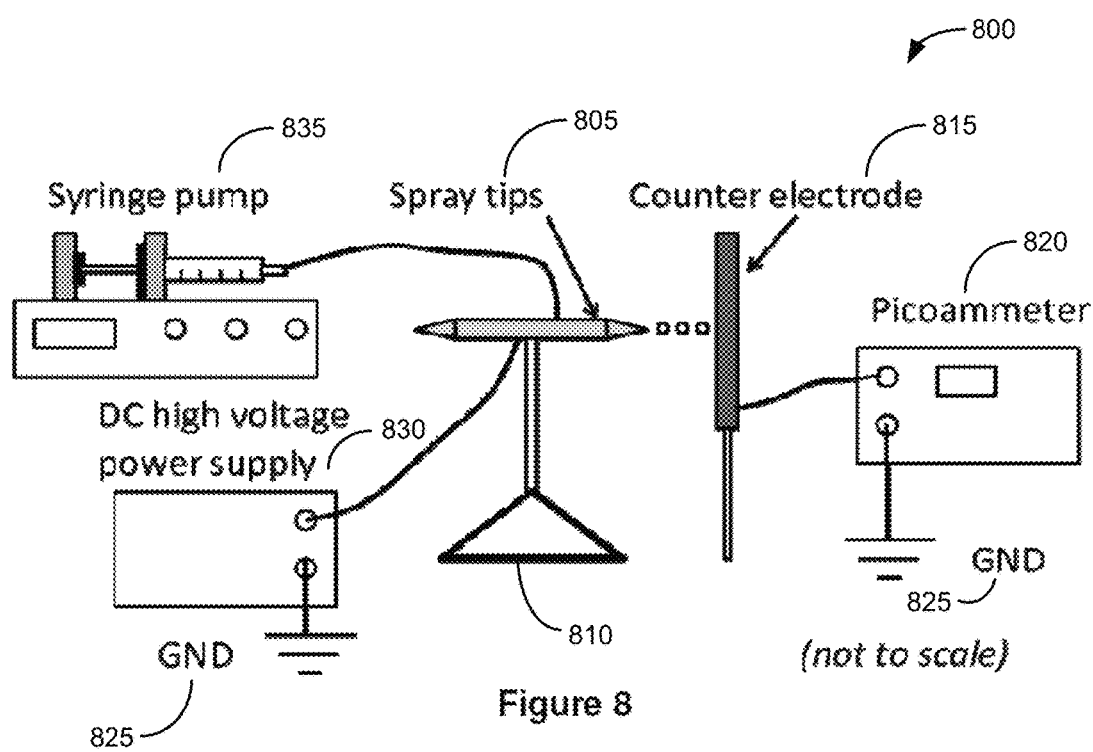
FIG. 8 shows schematics of the experimental setup 800 used for electrospray current measurements. Spray tips 805 were placed on a translational stage 810 with their protruding nozzles perpendicular to a stainless steel disk as the counter electrode 815. The disk 815 was connected to a picoammeter 820, which shared the electric ground 825 with the DC high voltage power supply 830 connected to the spray tips 805. A syringe pump 835 provided direct sample infusion into the spray tips 805.

Total electrospray currents were measured using the Keithley 6487 Picoammeter with built-in data acquisition capabilities (Keithley Instruments). The experimental setup is shown in FIG. 8 and similar to what had been described.[27] Electrospray images were taken using a Waters nanoflow camera kit equipped with a MLH-10× microscope (Computar), and using a digital camera Nikon 3700 (Nikon Inc.) mounted on a 6×16$_{monocular}$ (Specwell Corp.).

Nanoelectrospray Mass Spectrometry

All electrospray MS experiments were performed on a hybrid quadrupole/orthogonal Q-TOF API US mass spectrometer (Waters Corp.) as described.[28] The MEA chip was mounted on the voltage stand and manually rotated every 3-4 degrees for each adjacent emitter. MEA chips were connected with fused silica capillaries (o.d. ~360 μm, i.d. ~100 μm) by polytetrafluoroethylene (PTFE) tubing whose outer diameter (o.d.) matches the i.d. of access holes. Torr Seal epoxy (Agilent Technologies) was applied to permanently seal the connection which could withstand a pressure of more than 100 psi. An aluminum conductive tape (3M) provided the direct electric contact between the voltage stand and the conductive Si-based MEA chip.

Liquid Chromatography-MS/NIS

LC-MS/MS analysis was performed using a capillary liquid chromatography system (CapLC) (Waters Corp.) interfaced with a Q-TOF API US mass spectrometer as described.[28] LC runs using the same C18 column were performed sequentially and independently for individual multinozzle emitters. Peptides eluted from the column were directed through a connecting PTFE tubing (i.d. ~75 μm, o.d. ~1.6 mm) to the Picotips or MEA emitters for nanoelectrospray mass spectrometry. Mass spectra were processed using the MassLynx 4.0 SP4 software. Proteins were identified by Mascot (http://www.matrixscience.com) using the MS/MS peak lists exported from the MassLynx.

Design and Fabrication of MEA Chips

All components and their layout on the MEA chips (FIG. 1a) were designed using the L-Edit software (v15, Tanner Research Inc., Monrovia, Calif.). The procedures to fabricate the MEA chips were improved from those for $M^3$ emitters[1] and involved 9 major steps (FIG. 6a-i). First, we performed standard photolithography and deep reactive ion etching (DRIE) to pattern and produce channels (with micropillar arrays if needed) and emitters on a 4-inch silicon wafer (a-c). Then, we performed second-layer photolithography and DRIE to define and create access holes with a second film mask (d). The through-holes provided the opening for oxidant species to reach the sealed channel surface in the following steps. Next, we performed thermal fusion bonding between the patterned wafer and another clean wafer (e). The wafers were brought into contact to form spontaneous bonding followed by annealing in the furnace, with $N_2$ flow at 1050° C. for 1 hour, to generate covalent fusion bonding. Next, we performed wet oxidation to grow a thick oxide of ~1 μm on all silicon surfaces including the sealed channels/emitters (f). Afterwards, we performed another photolithography and through-wafer etching steps to sharpen the emitters (left- and right-side, FIG. 1 and FIG. 2) and release the chip from the wafer (g). The remaining photoresist after etching were removed by oxygen plasma instead of piranha cleaning. Otherwise, piranha solution tended to dissolve photoresist and clog the channels. Subsequently, we sharpened the other two sides (top and bottom, FIG. 1 and FIG. 2) of the emitters by mechanically polishing the emitter stem with the sand paper (h). Finally, we etched away silicon at the sharpened end of the emitters by selective $XeF_2$ etching (i). This final step ended up with protruding nozzles made of $SiO_2$. The nozzle length was controlled by tuning the $XeF_2$ etching cycles. To fabricate freestanding sharpened-end $M^3$ emitters, we followed the same procedures as described previously for $M^3$ emitters[26], but introduced an extra polishing step: after the individual emitters were diced from the silicon wafer, they were sharpened on all four edges at one end with the sand paper using a mechanical polishing station, cleaned with a piranha bath, followed by deionized water rinse and $N_2$ gas blow dry. The fabricated devices were examined by optical microscopy using a Reichert-Jung Polylite 88 microscope (Reichert Microscope Services, Depew, Calif.), and by scanning electron microscopy (SEM) using a JEOL 6340F FEG-SEM (JEOL Ltd., Tokyo, Japan). Safety considerations: All fabrication procedures were done in the class 100 cleanroom and hence the safety rules and laboratory protocols such as proper handling of toxic chemicals (particularly piranha and HF) must be followed at all times.

The back pressure of the emitters increased with the decrease in nozzle cross sections. This was due to the dramatic increase of hydrodynamic resistance (R), which is roughly inversely proportional to the fourth power of the nozzle diameter (D) (using Hagen-Poiseuille equation for square nozzles: $R \approx 128 \mu L/\pi D^4$, $\mu$ is viscosity and L is nozzle length); as well as the significant increase of pressure barrier ($\Delta P$) for liquid leakage in microfluidic channels, as estimated by $\Delta P = -2\gamma \cos \theta \cdot (1/h + 1/w)$, where $\gamma$ and $\theta$ are surface tension of the liquid and the contact angle between the liquid and channel walls, respectively, while h and w are channel height and width, respectively[29].

Electrostatic Simulations of MEA Emitters

The multiphysics modeling and simulation software COMSOL (v4.1, COMSOL Inc., Burlington, Mass.) was used to simulate electric fields of MEA emitters with different sharpened features (FIG. 2). For simplicity, we did not take into account the presence of complex dynamic gas/fluid behaviors during the actual electrospray process, and only considered static electric fields on MEA emitters relative to the Z-spray sample cone of the Q-TOF API US mass spectrometer (Waters Corp., Milford, Mass.). Furthermore, we simulated a quadrant instead of the whole device to reduce the dimensions of modeling. Briefly, the static electric field, $E = -\nabla V$, was calculated by solving the classical Poisson's equation $-\nabla \cdot (\epsilon_0 \epsilon_r \nabla V) = \rho$, using the 3D electrostatic module, in which $\epsilon_0$ is the permittivity of free space, $\epsilon_r$ is the relatively permittivity, V is electric scalar potential, and $\rho$ is the space charge density. The simulation involved five major steps: 1. modeling geometry; 2. setting boundary conditions and subdomains; 3. generating mesh; 4. computing solutions; and 5. performing post-processing and visualization. The 3D geometry was constructed with the parameters similar to the actual experimental setup. The dimensions of the sample cone were 5 mm of base radius, 0.5 mm of top radius, and 5 mm of height. The voltage of the stainless steel cone was set at 40 V. The MEA chip had a radius of 40 mm and a thickness of 1 mm. The MEA emitters were equally spaced radially with an angle of 3.75° between adjacent ones. Each emitter consisted of 10 protruding $SiO_2$ nozzles with inter-nozzle distance of 40 μm. The nozzles had a cross-section of 10 μm×10 μm and a protruding length of 200 μm. The electric potential of 3 kV was applied to both the Si device and the $SiO_2$ nozzles, because in real experiments the nozzles were filled with sample solutions and became as conductive as the silicon material. The sample cone and MEA chip were placed in such a way that their central planes (z=0) matched. Zero surface charge was applied to the outer surfaces of the cuboid of 55 mm×55 mm×11 mm, which defined the dimension of our modeling. Three types (flat-end, two-side sharpened-end, and four-side sharpened-end) of MEA emitters were simulated to compare the sharpening effects on electric fields of emitter nozzles. The sharpening angles for the left/right side and top/bottom side were 15° and 8°, respectively. Calculated electric fields were analyzed by 3D slice plots on the central plane (z=0). For simplicity, the simulation was done for 1 atm ambient air under the room temperature (25° C.).

Electrospray Current Measurement of MEA Emitter

Total electrospray currents were measured using the Keithley 6487 Picoammeter with built-in data acquisition capabilities (Keithley Instruments, Cleveland, Ohio). The schematics of the experimental setup 800 is shown in FIG. 8 and similar to what was described[27]. Spray tips 805 (Picotips and MEA emitters) were mounted on a translational stage 810 and connected to a dc high-voltage power supply 830. A stainless steel disk (3 cm in diameter) as the counter electrode 815 was positioned and fixed at 2.5 mm from the spray tips 805 with the electrospray axis perpendicular to the disk plane. This disk 815 was directly connected to the picoammeter 820. A syringe pump 835 (Harvard Apparatus, Holliston, Mass.) for direct sample infusion was connected to the spray tips 805 through capillary fittings. A solvent mixture of 50:50 methanol/water+1% acetic acid was infused at different flow rates including 0.1, 0.2, 0.4, 0.6, and 1.0 μL/min. The voltage applied to the spray tips ranged from 1.0 kV to 4.8 kV. Each electrospray current under different flow rates and voltages was obtained by averaging 200 consecutive measurements. Standard deviation (s.d.) was calculated for 3-5 individual emitters. Electrospray images were taken using a Waters nanoflow camera kit equipped with a MLH-10× microscope (Computar, Commack, N.Y.), and using a digital camera Nikon 3700 (Nikon Inc., Melville, N.Y.) mounted on a 6×16$_{monocular}$ (Specwell Corp., Tokyo, Japan). Safety considerations: High voltages supplies should be handled with caution when in use. Solvents containing methanol and acetic acid were handled under the fume hood.

Nanoelectrospray Mass Spectrometry

All electrospray MS experiments were performed on a hybrid quadrupole/orthogonal Q-TOF API US mass spectrometer (Waters Corp., Milford, Mass.). The mass spectrometer was operated in a positive ion mode with a source temperature of 120° C. and a cone voltage of 40 V. A voltage of 1-5 kV was applied to the MEA emitters or Picotip emitters (i.d. ~10 μm at the tip) (New Objectives Inc., Woburn, Mass.). The MEA chip was mounted on the voltage stand and manually rotated every 3-4 degrees for each adjacent emitter. TOF analyzer was set in the V-mode. The instrument was calibrated with a multi-point calibration using selected fragment ions from the collision-induced dissociation (CID) of Glu-fibrinopeptide B, GFP B (Sigma, St. Louis, Mo.). Electrical contact between the voltage stand and MEA chips was made via an aluminum conductive tape. MEA chips were connected with fused silica capillaries (o.d. ~360 μm, i.d. 100 μm) by polytetrafluoroethylene (PTFE) tubing whose outer diameter (o.d.) matches the i.d. of the access holes (FIG. 1b). Torr Seal epoxy (Agilent Technologies, Santa Clara, Calif.) was applied to permanently seal the connection which could withstand a pressure of more than 100 psi. To test the sensitivity and stability of the emitters, GFP B at a concentration of 0.1 or 1 pmole/μL in a solvent mixture of 50/50 acetonitrile/$H_2O$+0.1% formic acid was infused directly with a syringe pump at a flow rate of 0.6 μL/min. Data was acquired at 2.4 seconds per scan with 0.1 second between scans. Safety considerations: High voltages applied in the mass spectrometer should be exercised with caution. Solvents containing acetonitrile and formic acid were handled under the fume hood.

Liquid Chromatography-MS/NIS

LC-MS/MS analysis was performed using a capillary liquid chromatography system (CapLC) (Waters Corp.) interfaced with a Q-TOF API US mass spectrometer as described[28]. Briefly, 100 fmole of tryptic digests of bovine serum albumin (Michrom Bioresources, Auburn, Calif.) were injected into the CapLC system through an autosampler, pre-concentrated in a 300 μm (i.d.)×5 mm pre-column packed with PepMap C18 resin (particle diameter of 5 μm and pore size of 100 Å) (Dionex Corp., Sunnyvale, Calif.), and separated in a 75 μm (i.d.)×15 cm analytical column packed with the same PepMap C18 resin. The column was equilibrated with solution A containing 3% acetonitrile/97% water/0.1% formic acid, and the peptide separation was achieved with a gradient from 3% to 40% of solution B (95% acetonitrile/5% water/0.1% formic acid) over 32 mins (i.e., from 3 min to 35 min) at a flow rate of ~250 nL/min. This flow rate was achieved by splitting of the 8 μL/min flow from pumps A and B. Peptides eluted from the column were directed through a connecting PTFE Teflon tubing (i.d. ~75 μm, o.d. ~1.6 mm) to the Picotips or MEA emitters for nanoelectrospray mass spectrometry.

MS/MS spectra were obtained in a data-dependent acquisition (DDA) mode in which the three multiple-charged (+2, +3, +4) peaks with the highest intensity in each MS scan were chosen for CID. Collision energies were set at 10 eV and 30 eV during the MS scan and MS/MS scans, respectively. MS survey scan was 1 second per scan with an inter-scan delay of 0.1 second, while MS/MS scan was 1.9 seconds per scan with an inter-scan delay of 0.1 second. Mass spectra were processed using the MassLynx 4.0 SP4 software. Proteins were identified by Mascot (http://www-.matrixscience.com) using the MS/MS peak lists exported from the MassLynx. Protein modifications considered in the search included carboxymethylation of cysteine, N-terminal acetylation, N-terminal Gln to pyroGlu, oxidation of methionine, and phosphorylation of serine, threonine, and tyrosine.

Results and Discussions

Multinozzle Emitter Arrays

We developed MEAs consisting of 96 identical multi-nozzle emitters in a circular array, uniformly distributed on the periphery of a 3-inch silicon chip (FIGS. 1a and 1b). We designed the array layout and inter-emitter spacing in such a way to achieve the best electrospray performance possible while maximizing the number of emitters on the device. Notably, our fabrication processes are amendable for higher-number emitter arrays, e.g., 384 emitters on 6-inch Si wafers.

We utilized sharpened-end features at the four edges (left, right, top, and bottom) of each emitter in order to obtain enhanced electric fields (discussed in the next section). Each emitter was connected to off-chip components via capillaries through its access hole. This is a straightforward design compatible with majority of the microfluidic systems. FIG. 1b shows a representative optical image of a MEA chip with 96 emitters individually connected to capillaries for sample injection. FIGS. 1c, 1d, and 1e show SEM images for three adjacent emitters, a single 10-nozzle emitter, and the micropillar arrays monolithically imbedded in the main channel of each emitter, respectively. The micropillar arrays will be utilized in the future for online digestion (e.g., with trypsin coating) or separation (e.g., with C18 or C4 coating) after surface derivatization using silylation chemistry.

Figure 7:
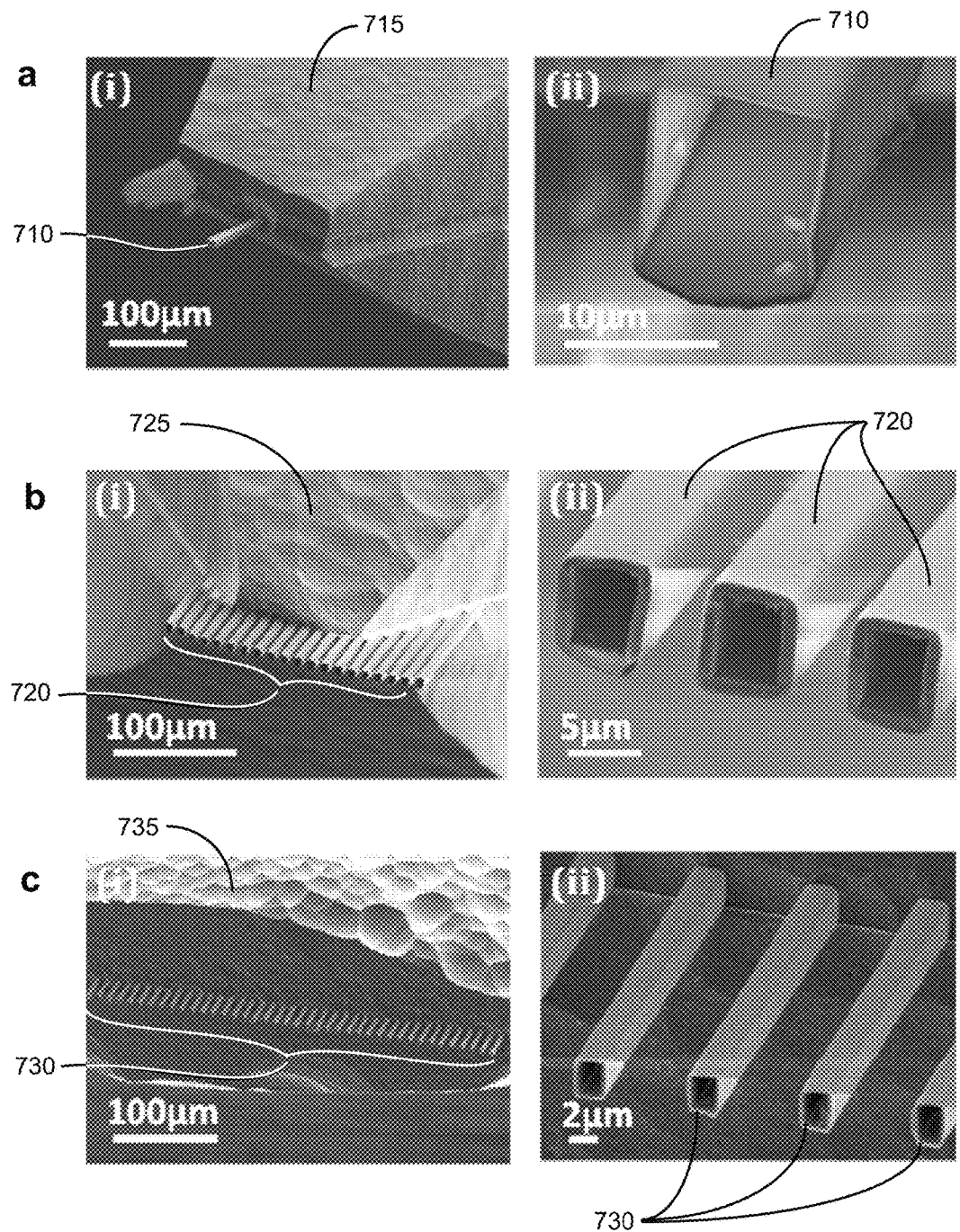
FIG. 7 shows SEM images of sharpened-end multinozzle emitters. (a) 1-nozzle 710 emitter 715 with a cross-section of 10 µm×10 µm. (b) 20-nozzle 720 emitter 725 with a cross-section of 5 µm×5 µm. (c) 40-nozzle 730 emitter 735 with a cross-section of 2 µm×2.5 µm. The zoom-out and close-up views of each emitter are shown in the panels (i) and (ii), respectively.

We fabricated emitters with varied nozzle numbers, cross-sections, and wall-thickness. FIG. 7 shows three representative sharpened-end emitters with a nozzle cross-section ranging from 10 μm×10 μm to 2 μm×2.5 μm, and the corresponding nozzle number per emitter from 1 to 40. We were able to fabricate nozzles with a cross-section down to ~800 nm×800 nm (data not shown), but a significant increase of back pressure[29] prevented us from utilizing these small nozzles for ESI-MS. We have mainly examined the performance of multinozzle emitters with a nozzle cross-section of ~10 μm×10 μm in this work. The potential of using smaller nozzles will be explored in the future.

We achieved a fabrication yield close to 100% for MEA emitters due to the significantly-improved microfabrication processes. For our $M^3$ emitters, sealed main channels were opened up by mechanical sawing, which resulted in serious clogging.[26] The fabrication of MEA emitters did not involve the mechanical dicing step. Instead, main channels were opened up by deep reactive ion etching, which is a dry etching process that does not introduce any particles into the main channels. The mechanical polishing step with the sand paper (Step h) typically generates particles larger than the nozzle sizes (e.g., 10 μm), which are removed by piranha cleaning. Therefore, our new procedures dramatically reduced channel clogging and improved device yields. Additionally, the connection between the MEA chip and outside liquid sources can be improved, by building a custom-made manifold which mechanically assembles the chip with tubings, O-rings, and/or gaskets. This manifold can withstand high pressures and be reused, and also minimizes dead volumes.

Electric Fields on the Multinozzle Emitter Arrays

Figure 3:
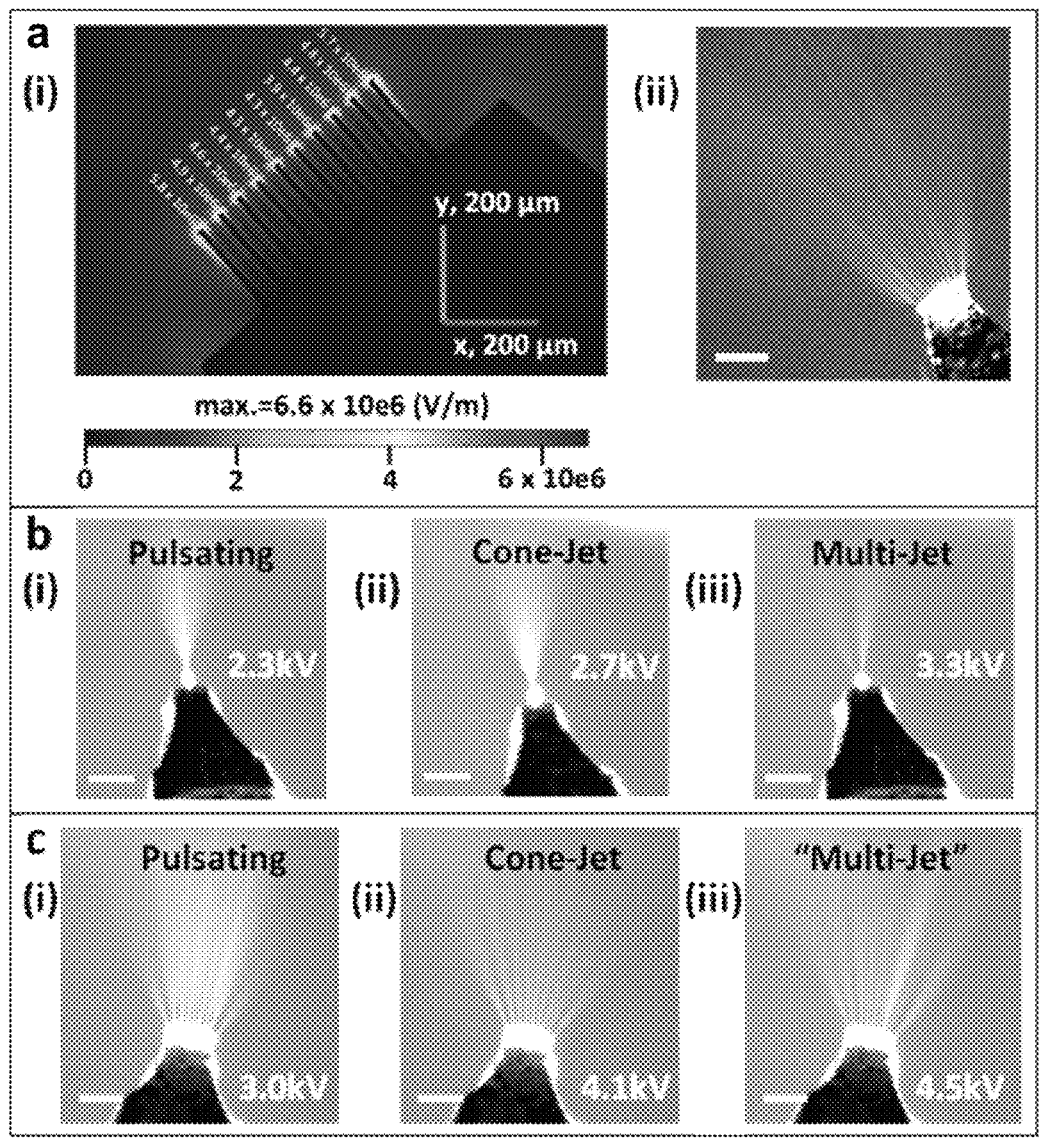
FIG. 3 shows electrospray modes on MEA chips. (a) Comparison between electrostatic simulation and electrospray on a MEA chip. (a-i) representative values of the simulated electric fields at the center of each nozzle, on a four-side sharpened-end 10-nozzle MEA emitter. The voltages and the relative geometry for the ion cone and the MEA chip are the same as in FIG. 2c. (a-ii) corresponding electrospray images for the 10-nozzle MEA emitter. Electrospray was performed using 50% methanol/$H_2O$+0.1% formic acid at a flow rate of 3.0 µL/min. (b) Electrospray images of 1-nozzle MEA emitters at the flow rate of 0.6 µL/min, showing the (b-i) pulsating (2.3 kV), (b-ii) cone-jet (2.7 kV), and (b-iii) multi-jet (3.3 kV) modes. (c) Electrospray images of 10-nozzle MEA emitters at the flow rate of 1.0 µL/min, showing the (c-i) pulsating, (c-ii) cone-jet, and (c-iii) "multi-jet" modes at indicated voltages. The images were taken using the setup for electrospray current measurements. The solvent was 50% methanol/$H_2O$+1% acetic acid. All nozzles have a cross-section of 10 µm×10 µm. Scale bars in a-c are 500 µm.

We utilized a 3D electrostatic simulator to examine the effects of sharpened-end features on the electric fields of emitters. Three types of emitters with the same number of nozzles (i.e., 10) including those for flat-end (FIG. 2a), two-side sharpened-end (FIG. 2b), and four-side sharpened-end (FIG. 2c), were compared. The electric fields were much stronger at the nozzle tips than in the other regions of the emitters for all three cases. But the maximum of the electric fields at the nozzle tips significantly increased from $3.7 \times 10^6$ V/m for the flat-end emitters to $6.6 \times 10^6$ V/m for the four-side sharpened-end emitters. For each emitter, we observed higher electric fields at the tips of the periphery nozzles than those of the interior ones. In particular, there was a gradual increase from the center to the edge of the linear nozzle array, with a maximum increase of 48.7% from the center nozzle ($3.9\times10^6$) to the edge nozzle ($5.8\times10^6$) for the four-side sharpened-end emitters (FIG. 2c(iii) and FIG. 3a). This was due to the linear format of the nozzle array, the position of the nozzle array relative to the ion cone (Z-spray), the nozzle-nozzle interactions (shielding effects),[30] and the interactions between the emitter stem and the nozzles on the two edges (i.e., the edge effects). Consistently, we observed even higher electric fields at the corner of the nozzles on two edges, i.e., $6.6\times10^6$ (left corner, not labeled) vs. $5.8\times10^6$ (center, labeled) for the leftmost nozzle; and $6.1\times10^6$ (right corner, not labeled) vs. $5.7\times10^6$ (center, labeled) for the rightmost nozzle, respectively (FIG. 3a). We further confirmed the simulated pattern of the electric fields experimentally. As demonstrated by the electrospray images of a corresponding 10-nozzle MEA emitter, the spray plumes showed a clear edge effect for the outmost nozzles while relative homogeneity among the inner nozzles (FIG. 3b).

Although enhancement of electric fields at sharp tips is a known phenomenon, ours is one of the first examples showing increased electric fields at the nozzles through sharpening the emitter stems instead of the nozzles themselves for Si-based devices. The protruding feature of the nozzles prevented sample wetting on the emitter surface, while the sharpening of the emitter stems ensured sufficient electric fields for Taylor cone formation. It is expected that additional improvement could be achieved by optimizing the shape of the nozzle support (e.g., sharpening angles for four sides), and the 3D layout of the nozzles (e.g., a circular array). The same modeling strategy is applicable for rational design of microfluidic modules.

Electrospray Currents of Multinozzle Emitter Arrays

We compared the total electrospray currents over a wide range of applied voltages and flow rates for 1- and 10-nozzle MEA emitters and Picotips. As shown in FIG. 4a, electrospray current for 1-nozzle MEA emitter reached two plateau regions at ~2.3 kV and ~2.7 kV, respectively. Concurrently, we observed three electrospray modes including pulsating (2.3 kV), cone-jet (2.7 kV), and multi-jet (3.3 kV) (FIG. 3b), similar to those described for capillary and elastomeric emitters.[31, 32] For 10-nozzle MEA emitters, the constant-current plateau region (cone-jet mode) was observed at higher voltages of ~3.6 kV (FIG. 4b). However, its "multi-jet" mode was harder to observe due to the multi-spray nature of the multinozzle emitters (FIG. 3c). On the other hand, we observed comparable electrospray currents for 1-nozzle MEA emitter and Picotips under same conditions, although there was no clear plateau region for Picotips (data not shown).

We next tested whether our multinozzle emitters followed the square root n relationship, i.e., the total electrospray current from the multi-electrosprays in the cone-jet mode is proportional to the square root of the number of sprays (nozzles).[27, 32] We measured the dependence between total electrospray current and applied voltages for 1- and 10-nozzle MEA emitters at given total flow rates, shown in FIG. 4a for 0.6 μL/min. We then determined the electrospray current for a particular total flow rate at the plateau region corresponding to the cone-jet mode. As shown in FIG. 4b, the electrospray currents from both 1- and 10-nozzle MEA emitters fitted a power of the total flow rate, with the power constant of 0.47 and 0.48, respectively. This was consistent with the square root relationship between spray currents and total flow rates. Furthermore, at a given total flow rate, the ratio of electrospray currents between 10- and 1-nozzle MEA emitters was calculated to be 2.65~2.85 for the total flow rates of 0.2~0.6 μL/min (FIG. 4b insert), which was 10-20% less than the predicted theoretical ratio of 3.16, i.e., the square root of 10 (nozzles).[27, 32] The discrepancy might be due to the inhomogeneity among the 10-nozzles as exemplified by their electric field distribution (FIG. 3a), as well as the much stronger inter-nozzle interactions for 10-nozzle MEA emitters in comparison to a bundle of multiple capillary emitters[32]. In fact, both the size (a cross-section of ~10 μm×10 μm) and inter-nozzle spacing (~40 μm) of MEA emitters were significantly smaller than those of the bundle of fused silica capillaries (i.d. ~19 μm and the inter-capillary spacing of ~500 μm, respectively). In addition, there were inter-emitter interactions on MEA chips. Nevertheless, the significant increase of electrospray currents in 10-nozzle MEA emitters suggested the feasibility of achieving even higher MS sensitivity for multinozzle emitters with larger nozzle numbers.

High-Throughput Mass Spectrometry Using Multinozzle Emitter Arrays

We first confirmed that sharpening dramatically reduced operating voltages for ESI-MS using sharpened-end $M^3$ emitters (FIG. 9). Strikingly, optimal operating voltage was observed at ~1.8 kV for single-nozzle emitters, which was similar to those for Picotips (1.5 kV~2.3 kV), and a dramatic improvement from that for flat-end single-nozzle emitters (4.5 kV~4.8 kV).[26] For a sharpened-end 20-nozzle emitter, the optimal voltage was 3.5 kV, confirming the aforementioned inter-nozzle interactions.[30] We observed that both the optimal voltage and MS sensitivity increased with nozzle numbers. For example, there was an on average ~2-fold increase in sensitivity for the 20-nozzle relative to the 1-nozzle emitters. As mentioned above, electrospray current and therefore MS sensitivity was predicted to be proportional to the square root of the number of nozzles.[27] If this holds for our multinozzle emitters, one would expect about 4.5-fold increase. The difference was probably due to the suboptimal efficiency of ion collection and transmission by the Z-spray sample cone of our mass spectrometer, because electrosprays from multinozzle emitters were spread out significantly. Future implementation of a funnel-shaped sample cone[20] may increase MS sensitivity for multinozzle emitters.

Figure 4:
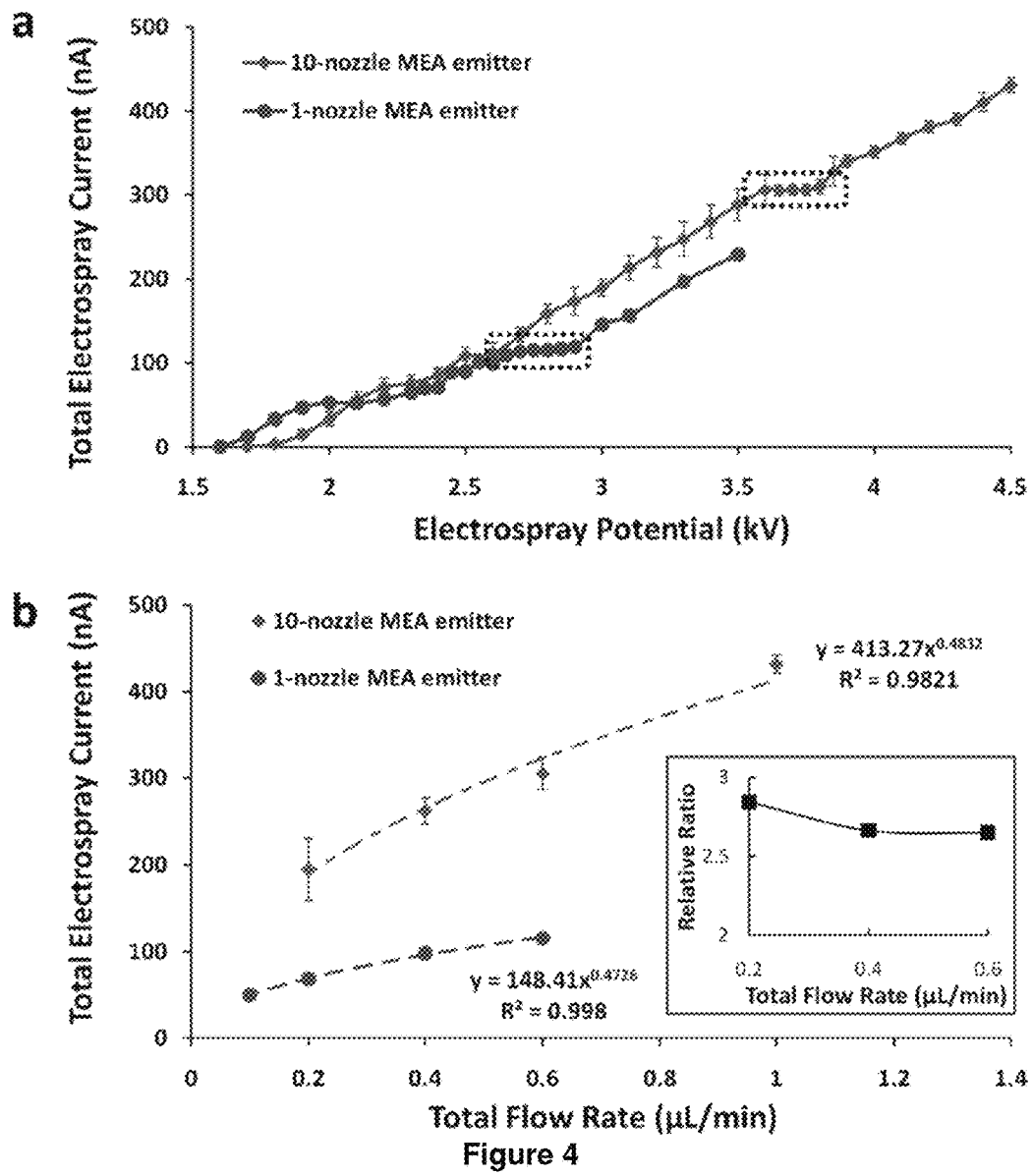
FIG. 4 shows electrospray currents of MEA emitters. (a) Representative curves of total electrospray currents for 1- and 10-nozzle MEA emitters, as a function of applied voltages at the total flow rate of 0.6 µL/min. The plateau regions of both curves designated by the dashed box indicate the cone-jet mode regimes for electrospray at this flow rate. (b) Comparison of total electrospray currents between 1- and 10-nozzle MEA emitters, spraying in the cone-jet mode regimes at different total flow rates. The values were fitted by a power-law function with the constant of 0.4726 and 0.4832 for 1- and 10-nozzle emitters, respectively. The inset shows the relative ratios between 10- and 1-nozzle MEA emitters as a function of total flow rates. All nozzles have a cross-section of 10 µm×10 µm. The solvent was 50% methanol/$H_2O$+1% acetic acid. Error bars: s.d., calculated for 3-5 individual emitters. The error bars for 1-nozzle MEA emitters were too small to display.

We next compared the performance of MEA emitters, free-standing sharpened-end $M^3$ emitters, and Picotips. All three types of emitters achieved comparably high MS sensitivity for 0.1 μM GFP (FIG. 5a,). We observed a slightly (~10%) higher MS sensitivity for both 10-nozzle MEA and $M^3$ emitters than Picotips. Importantly, both 10-nozzle MEA and $M^3$ emitters achieved higher MS sensitivity than their 1-nozzle counterparts, validating the value of the multinozzle design. However, the fold change was around 1.5-2.0 and less than what would be expected from the square root n relationship, i.e., ~3 fold, as shown by the electrospray current (FIG. 4). As discussed above, future optimization of both the MS ion optics and the relative position between MEA emitters and the ion cone (FIG. 5a insert) may mitigate this limitation. We achieved stable electrosprays at 3.5 and 4.5 kV for 1- and 10-nozzle MEA emitters, respectively, while at 1.8 and 3.2 kV for 1- and 10-nozzle sharpened-end $M^3$ emitters, respectively (FIG. 5a). This was presumably due to the emitter-emitter interactions on the MEA chip, in addition to the nozzle-nozzle interactions within an emitter encountered by both types of emitters. Therefore, an operating voltage higher than the maximum of 5.0 kV provided by our current Q-TOF mass spectrometer, is needed to for MEA emitters with even larger nozzle numbers (e.g., 40). We checked the MS stability for MEA emitters using 0.1 μM and 1.0 μM GFP, respectively. The relative standard deviation (RSD) for either 1- or 10-nozzle MEA emitters was similar to that of Picotips (FIG. 5b).

We further demonstrated the proof-of-principle applications of MEA emitters in high-throughput proteomics. FIG. 5c shows representative LC-MS/MS chromatograms for 100 fmole tryptic digests of bovine serum albumin (BSA, ~67 kDa), with one TOF MS (BPI, base peak intensity) each for one Picotip and 7 individual MEA emitters chosen randomly out of the 96 on a MEA chip. There was no significant difference among these chromatograms. In addition, BSA was confidently identified in all cases. With MEA emitters, we obtained on average a Mascot score of 1300 and 43% sequence coverage with 27 peptides sequenced, while for Picotip emitters a Mascot score of 1333 and 46% sequence coverage. The small discrepancy among MEA emitters presumably resulted from the slight difference in the positioning of each emitter relative to the ion cone of our mass spectrometer. This can be mitigated in the future through a computer-controlled rotary system optimized for the 3-inch MEA chip.

Our results demonstrated that MEA emitters could be interfaced with LC-MS/MS for sequential and reproducible high-sensitivity proteomic analyses. It is conceivable that multiple (up to 96) LC systems can be interfaced with our MEA chip to achieve, either sequential (if using only one mass spectrometer) or parallel (if using multiple, for example, miniaturized mass spectrometers[33, 34]), high-throughput MS analyses. More importantly, our MEA platform is ready for the high-level integration with additional functional modules, to achieve "Lab-on-a-chip". For example, the micropillar arrays embedded in the main channel can be utilized for digestion and separation. The fully-integrated system will dramatically increase the sensitivity and throughput for mass spectrometry-based metabolomics and proteomics, through efficient manipulation and processing of an extremely small amount of samples (such as a single cell), and by diminishing the processing time for cell manipulation, and protein digestion and separation, etc. Our platform can be further interfaced with other technologies such as femtoliter and picoliter-sized droplets for manipulating single cells.[35] Since our MEA chip is made of conductive Si, there is no liquid junction and conductive coating needed to establish the electric contact between voltage supplies and the chip. This added advantage simplifies the fluidic control on integrated MEA chips. Our design can be extended to MEAs with even higher emitter numbers (e.g., 384), thus enabling "ultrahigh-throughput". With further optimization, our MEA emitters will achieve even better performance in MS sensitivity and stability, thus enabling "ultrahigh-sensitivity".

Conclusions

By taking advantages of the maturity and flexibility of silicon microfabrication technologies, we demonstrate massively-parallel multinozzle emitters integrated uniformly in a circular array, enabling high-sensitivity and high-throughput nanoelectrospray mass spectrometry. Our MEA chip is the first silicon-based, robust, and microfabricated monolithic multinozzle emitters implemented in a high-throughput array format. Our MEA chip has multiple advantages. Firstly, it eliminates potential sample carryover because each sample will be analyzed by a different emitter. Secondly, it improves reproducibility for parallel analysis because emitters are identically microfabricated. Thirdly, due to the robustness and inert nature of silicon material, MEA chip can work under various conditions and be reused. Fourthly, the clogging at the nozzle tips due to salt and debris built-ups, typically encountered by the commercial Picotips, is significant mitigated due to the multinozzle design. In addition, a series of prefilters can be readily fabricated in the main channels to prevent large debris or particles from entering the nozzles and thereby effectively reduce the clogging. Fifthly, the throughput can be further improved by increasing the wafer size (e.g., from 4- to 6-inch) and optimizing the overall layout geometry. Lastly, the MS sensitivity can be further improved if emitters with an even larger number of nozzles are interfaced with optimized ion optics for efficient ion collection and transmission. In summary, we present the first demonstration of silicon-based monolithic multinozzle emitter arrays (MEAs) for nanoelectrospray mass spectrometry. Once integrated with other functional modules, our MEA chips have the potential to serve as a unified platform for future ultrahigh-sensitivity and ultrahigh-throughput proteomics and metabolomics.

REFERENCE (1) Wang, D.; Bodovitz, S. *Trends Biotechnol.* 2010, 28, 281-290.
(2) Whittal, R. M.; Keller, B. O.; Li, L. *Anal. Chem.* 1998, 70, 5344-5347.
(3) Rubakhin, S. S.; Sweedler, J. V. *Nat. Protoc.* 2007, 2, 1987-1997.
(4) Amantonico, A.; Urban, P. L.; Fagerer, S. R.; Balabin, R. M.; Zenobi, R. *Anal. Chem.* 2010, 82, 7394-7400.
(5) Lapainis, T.; Rubakhin, S. S.; Sweedler, J. V. *Anal. Chem.* 2009, 81, 5858-5864.
(6) Shrestha, B.; Vertes, A. *Anal. Chem.* 2009, 81, 8265-8271.
(7) Fenn, J. B.; Mann, M.; Meng, C. K.; Wong, S. F.; Whitehouse, C. M. *Science* 1989, 246, 64-71.
(8) Wilm, M.; Mann, M. *Anal. Chem.* 1996, 68, 1-8.
(9) Whitesides, G. M. *Nature* 2006, 442, 368-373.
(10) Sikanen, T.; Franssila, S.; Kauppila, T. J.; Kostiainen, R.; Kotiaho, T.; Ketola, R. A. *Mass Spectrom. Rev.* 2010, 29, 351-391.
(11) Licklider, L.; Wang, X. Q.; Desai, A.; Tai, Y. C.; Lee, T. D. *Anal. Chem.* 2000, 72, 367-375.
(12) Yang, Y.; Kameoka, J.; Wachs, T.; Henion, J. D.; Craighead, H. G. *Anal. Chem.* 2004, 76, 2568-2574.
(13) Kim, J. S.; Knapp, D. R. *J. Am. Soc. Mass Spectrom.* 2001, 12, 463-469.
(14) Schilling, M.; Nigge, W.; Rudzinski, A.; Neyer, A.; Hergenroder, R. *Lab Chip* 2004, 4, 220-224.
(15) Le Gac, S.; Cren-Olive, C.; Rolando, C.; Arscott, S. *J. Am. Soc. Mass Spectrom.* 2004, 15, 409-412.
(16) Hoffmann, P.; Eschner, M.; Fritzsche, S.; Belder, D. *Anal. Chem.* 2009, 81, 7256-7261.
(17) Mellors, J. S.; Jorabchi, K.; Smith, L. M.; Ramsey, J. M. *Anal. Chem.* 2010, 82, 967-973.
(18) Schultz, G. A.; Corso, T. N.; Prosser, S. J.; Zhang, S. *Anal. Chem.* 2000, 72, 4058-4063.
(19) Gibson, G. T.; Mugo, S. M.; Oleschuk, R. D. *Mass Spectrom. Rev.* 2009, 28, 918-936.
(20) Kelly, R. T.; Page, J. S.; Zhao, R.; Qian, W. J.; Mottaz, H. M.; Tang, K.; Smith, R. D. *Anal. Chem.* 2008, 80, 143-149.
(21) Su, S.; Gibson, G. T.; Mugo, S. M.; Marecak, D. M.; Oleschuk, R. D. *Anal. Chem.* 2009, 81, 7281-7287.
(22) Xue, Q.; Foret, F.; Dunayevskiy, Y. M.; Zavracky, P. M.; McGruer, N. E.; Karger, B. L. *Anal. Chem.* 1997, 69, 426-430.

(23) Liu, H.; Felten, C.; Xue, Q.; Zhang, B.; Jedrzejewski, P.; Karger, B. L.; Foret, F. *Anal. Chem.* 2000, 72, 3303-3310.
(24) Dayon, L.; Abonnenc, M.; Prudent, M.; Lion, N.; Girault, H. H. *J. Mass Spectrom.* 2006, 41, 1484-1490.
(25) Moini, M.; Jiang, L.; Bootwala, S. *Rapid Commun. Mass Spectrom.* 2011, 25, 789-794.
(26) Kim, W.; Guo, M.; Yang, P.; Wang, D. *Anal. Chem.* 2007, 79, 3703-3707.
(27) Tang, K.; Lin, Y.; Matson, D. W.; Kim, T.; Smith, R. D. *Anal. Chem.* 2001, 73, 1658-1663.
(28) Wang, D.; Park, J. S.; Chu, J. S.; Krakowski, A.; Luo, K.; Chen, D. J.; Li, S. *J. Biol. Chem.* 2004, 279, 43725-43734.
(29) Hosokawa, K.; Fujii, T.; Endo, I. *Anal. Chem.* 1999, 71, 4781-4785.
(30) Tatemoto, Y.; Ishikawa, R.; Takeuchi, M.; Takeshita, T.; Noda, K.; Okazaki, T. *Chem. Eng. Technol.* 2007, 30, 1274-1279.
(31) Marginean, I.; Kelly, R. T.; Page, J. S.; Tang, K.; Smith, R. D. *Anal. Chem.* 2007, 79, 8030-8036.
(32) Kelly, R. T.; Tang, K.; Irimia, D.; Toner, M.; Smith, R. D. *Anal. Chem.* 2008, 80, 3824-3831.
(33) Gao, L.; Song, Q.; Patterson, G. E.; Cooks, R. G.; Ouyang, Z. *Anal. Chem.* 2006, 78, 5994-6002.
(34) Malcolm, A.; Wright, S.; Syms, R. R.; Dash, N.; Schwab, M. A.; Finlay, A. *Anal. Chem.* 2010, 82, 1751-1758.
(35) Chiu, D. T.; Lorenz, R. M. *Acc. Chem. Res.* 2009, 42, 649-658.

Example 2

High-Density Microfabricated Multinozzle Emitters for Nanoelectrospray Mass Spectrometry We previously developed microfabricated monolithic multinozzle ($M^3$) emitters and demonstrated their applications in nanoelectrospray mass spectrometry[1]. However, the high operating voltage (4.5 kV) required for electrospray ionization prevented us from implementing high-density multinozzle emitters for mass spectrometry. Combining electrostatic simulation and experimental testing, we showed that sharpened-end geometry at the main channel of the $M^3$ emitters dramatically reduced the operating voltages for the multinozzles (to ~2-3.5 kV) in the cone-jet mode, comparable to that of commercial silica-based capillary nanoelectrospray tips. This critical improvement enabled us to fabricate and test $M^3$ emitters with high-density nozzle arrays (e.g., 20, 30, 40 nozzles with a linear density of 50~100 nozzles/mm). We showed increased mass spectrometry sensitivity of these emitters, with an average 3-fold increase for sharpened 20-nozzle emitters relative to the commercial tips. LC-MS/MS experiments using these emitters for protein identification further demonstrated their applications in proteomics. These sharpened multinozzle emitters constitute a critical step towards future $Si/SiO_2$-based systems for proteomics-on-a-chip.

Mass spectrometry (MS) is an enabling technology for proteomics and metabolomics[2, 3]. Electrospray ionization (ESI) mass spectrometry[4], particularly nano-ESI[5] mass spectrometry, remains the dominant method for analyzing complex mixtures of peptides and proteins. Rapid developments in mass spectrometers, coupled with label-free and stable-isotope labeling technologies, have driven the wide applications of mass spectrometry in qualitative and quantitative proteomics[6]. The "holy grail" of the field is to profile proteome and metabolome at the single cell level. Revolutionary innovations are needed to ultimately achieve this goal. Lab-on-a-chip may contribute to this endeavor due to its efficient manipulation of extremely small amount of samples (e.g., fL to nL) through micro/nanofluidics[7-11].

One of the key challenges has been to implement high-quality interface between microfluidic chips and mass spectrometers[12, 13]. The current focus[13] on the chip-ESI-MS interface has been on fully integrated microfabricated emitters, evolving from earlier and less robust off-the-edge spraying or inserted fused-silica capillary emitters. Both polymeric materials and silicon/silica-based emitters have been fabricated. The former included nozzles made of parylene[14, 15], poly(dimethylsiloxane)[16], poly(methyl methacrylate)[17], and a negative photoresist SU-8[18]. The latter includes nozzles made of silicon using out-of-plane processes[19]. However, hydrophobic polymers have inherently undesirable properties for the electrospray application, such as strong affinity to proteins and incompatibility with certain organic solvents[20, 21]. Out-of-plane fabrication is critically limited in terms of the flexibility to produce monolithically integrated built-in structures, and requires additional assembly steps to attach nozzles to the end of a microfluidic channel.

Another current interest is to develop multiple parallel electrosprays for mass spectrometry, in order to improve sensitivity and/or throughput. For example, higher-sensitivity multiple sprays were achieved with a bundle of fused silica capillaries[22]. Multiple electrospray has also been shown for an array of metal holes[23], silicon/silica nozzle arrays[24], and multi-capillary metal nozzles[25]. But all these fabricated devices have sizes in the range of millimeters to centimeters and are much bigger than conventional capillary nanoelectrospray emitters. This renders them unsuitable for potential mass spectrometry applications with conventional mass spectrometers. Furthermore, there has been no report on monolithic integration of multiple electrosprays for mass spectrometry on a chip, particularly for silicon/silica-based chips.

We have recently designed and produced microfabricated monolithic multinozzle emitters ($M^3$ emitters) using conventional in-plane silicon/silica fabrication technologies, and have further demonstrated their applications in nano-electrospray ionization mass spectrometry (nano-ESI-MS)[1]. However, the relatively high operating voltage (≥4.5 kV) required for the low-density $M^3$ emitters (up to 5 nozzles) remained problematic. This prevented us from implementing high-density nozzle array emitters (>10 nozzles) for mass spectrometry. It was shown that as the number of nozzles increased for a multi-capillary nozzle emitter consisting of one metal plate (30 mm in diameter) with capillary nozzles, a much higher voltage (e.g., 12.5 kV vs. 5.5 kV) was required to obtain a steady cone-jet mode electrospray (as compared to drip mode and multi-jet mode) because of the inter-nozzle interactions[25]. Therefore, one straightforward way to generate electrospray ionization for our previous multinozzle emitters is to proportionally increase the operating voltage for emitters with a larger number of nozzles. Nevertheless, the maximum voltage for the electrospray source for almost all current commercial mass spectrometers is around 4-5 kV (depending on the manufacturers and models). Furthermore, with higher voltages come with the drawbacks of unpredictable dissociation and ionization of biomolecules, and electric arcs between the emitters and counter electrodes (e.g., sample cones), which may damage the mass spectrometers.

Herein, we report a novel and straightforward approach to achieve the cone-jet mode electrospray ionization with relatively low voltages for high-density multinozzle emitters. Combining theoretical modeling with experimental testing, we demonstrated that the sharpened $M^3$ emitters could be subjected to a much higher electric field than their flat counterparts if applied with the same operating voltages. We further showed improved sensitivity for nanoelectrospray mass spectrometry and demonstrated proteomics applications of these high-density sharpened multinozzle emitters.

Experimental Section

Microfabrication of Sharpened $M^3$ Emitters.

The procedures to fabricate the flat-end $M^3$ emitters were essentially the same as we described previously[1]. High-density nozzle arrays were fabricated in the current work. The emitters consist of an array of 1, 5, 10, 20, or 40 spray nozzles (~2 or 10 μm in width, ~2 or 10 μm in depth, and ~200 μm in length) and a connecting microfluidic channel (~400 μm in width and ~6 cm in length). To fabricate the sharpened-end emitters, we introduced an extra polishing step. After the individual tips were diced from the silicon wafer, they were sharpened on all four edges at one end using a mechanical polishing station, and cleaned with a 120° C. piranha bath for 10 minutes followed by deionized water rinse and $N_2$ gas blow dry. Finally, the exposed silicon at the sharpened end of the tips was selectively etched away against $SiO_2$ using $XeF_2$ as the etching gas. This step left behind protruding nozzles made of $SiO_2$ (length ~200 μm). The resulted $M^3$ emitters were examined with optical microscopy using a Reichert-Jung Polylite 88 microscope (Reichert Microscope Services, Depew, Calif.), and scanning electron microscopy (SEM) using a JEOL 6340F FEG-SEM (JEOL Ltd., Tokyo, Japan).

Electrostatic Simulation of $M^3$ Emitters.

Electric fields at the $M^3$ emitters relative to the sample cone of the Z-spray of the Q-TOF mass spectrometer (Waters Corp., Milford, Mass.) were simulated using FEMLAB (COMSOL Inc., Burlington, Mass.). Briefly, the static electric field, $E=-\nabla V$, is calculated by solving the classical Poisson's equation $-\nabla \cdot (\epsilon_0 \epsilon_r \nabla V) = \rho$, using the 3D electrostatics application mode, in which $\epsilon_0$ is the permittivity of free space, $\epsilon_r$ is the relatively permittivity, V is electric scalar potential, and ρ is the space charge density. The simulation involved five major steps: 1. modeling geometry; 2. setting boundary conditions and subdomains; 3. generating mesh; 4. computing solutions; 5. post-processing and visualization. The 3D geometry was constructed with parameters from the actual experimental setup. The dimension of the sample cone used: base radius: 3 cm, top radius: 0.5 mm, and height: 1.5 cm. The stainless steel cone was set at 40 V and was at 90 degree angle relative to the $M^3$ emitters. Flat and sharpened single-nozzle $M^3$ emitters, consisting of a Si emitter (1 mm×1.5 mm×5 mm) with a protruding $SiO_2$ single nozzle (10 μm×10 μm×200 μm), were used in the modeling. A 3 kV electric potential was applied to the Si emitter while the continuity condition was applied to the $SiO_2$ nozzle. Zero surface charge was applied to the six outer surfaces of the overall system box (2 cm×2 cm×2 cm). For simplicity, the simulation was done for 1 atm ambient air under room temperature (25° C.) and did not take into account the presence of complex dynamic gas/fluid behaviors during the actual electrospray process.

Nanoelectrospray Mass Spectrometry and LC-MS/MS.

All electrospray ionization mass spectrometry experiments were performed on a Q-TOF mass spectrometer as described previously (Waters Corp., Milford, Mass.)[1]. To test the sensitivity and stability of the $M^3$ emitters, Glu-Fibrinopeptide B (GFP B) (Sigma, St. Louis, Mo.) at a concentration of 1 pmole/μl in 50% acetonitrile/0.1% formic acid was infused directly with a syringe pump. The mass spectrometer was operated in a positive ion mode with a source temperature of 120° C. and a cone voltage of 40 V. A voltage of 1-5 kV was applied to the $M^3$ emitters. TOF analyzer was set in the V-mode. The instrument was calibrated with a multi-point calibration using selected fragment ions from the collision-induced decomposition (CID) of GFP B. Data was acquired at 2.4 seconds per scan with 0.1 second between scans. Images and videos of the electrospray process were taken by a digital camera (Nikon 3700, Nikon Inc., Melville, N.Y.) mounted on a 6×16 Specwell monocular (Specwell Corp., Tokyo, Japan).

LC-MS/MS analysis was performed using a capillary liquid chromatography system (Waters Corp.) interfaced with the Q-TOF mass spectrometer as we described in detail[26]. Briefly, 100 fmole of tryptic digests of bovine serum albumin (Michrom Bioresources, Auburn, Calif.) were injected into the LC system through an auto-sampler, pre-concentrated on a 300 μm (i.d.)×5 mm precolumn packed with PepMap C18 resin (particle diameter, 5 μm; pore size, 100 A) (Dionex Corp., Sunnyvale, Calif.), and separated on a 75 μm (i.d.)×15 cm analytical column packed with the same PepMap C18 resin. The column was equilibrated with solution A (3% acetonitrile, 97% water, 0.1% formic acid), and the peptide separation was achieved with a solution gradient from 3 to 40% of solution B (95% acetonitrile, 5% water, 0.1% formic acid) over 32 mins (3 min to 35 min) at a flow rate of ~250 nl/min. This flow rate through the column was reduced from 8 μl/min from pumps A and B by flow splitting. The LC eluent from the column was directed through the connecting PTFE Teflon tubing (i.d. ~75 μm, o.d. ~1.6 mm) to the $M^3$ emitters for nanoelectrospray mass spectrometry. Epoxy adhesive was applied to seal the connection and was cured overnight at room temperature before use.

MS/MS spectra were obtained in a data-dependent acquisition (DDA) mode in which the three multiple-charged (+2, +3, +4) peaks with the highest intensity in each MS scan were chosen for CID. Collision energies were set at 10 V and 30 V respectively during the MS scan and MS/MS scans. MS survey scan was 1 second per scan with an inter-scan delay of 0.1 second, while MS/MS scan was 1.9 seconds per scan with an inter-scan delay of 0.1 second. Mass spectra were processed using MassLynx 4.0 SP4 software. Proteins were identified by Mascot (http://www.matrixscience.com) using the MS/MS peak lists exported from the MassLynx. Protein modifications considered in the search included carboxymethylation of cysteine, N-terminal acetylation, N-terminal Gln to pyroGlu, oxidation of methionine, and phosphorylation of serine, threonine, and tyrosine.

Results and Discussions

Electric Field Simulation for $M^3$ Emitters.

Figure 10:
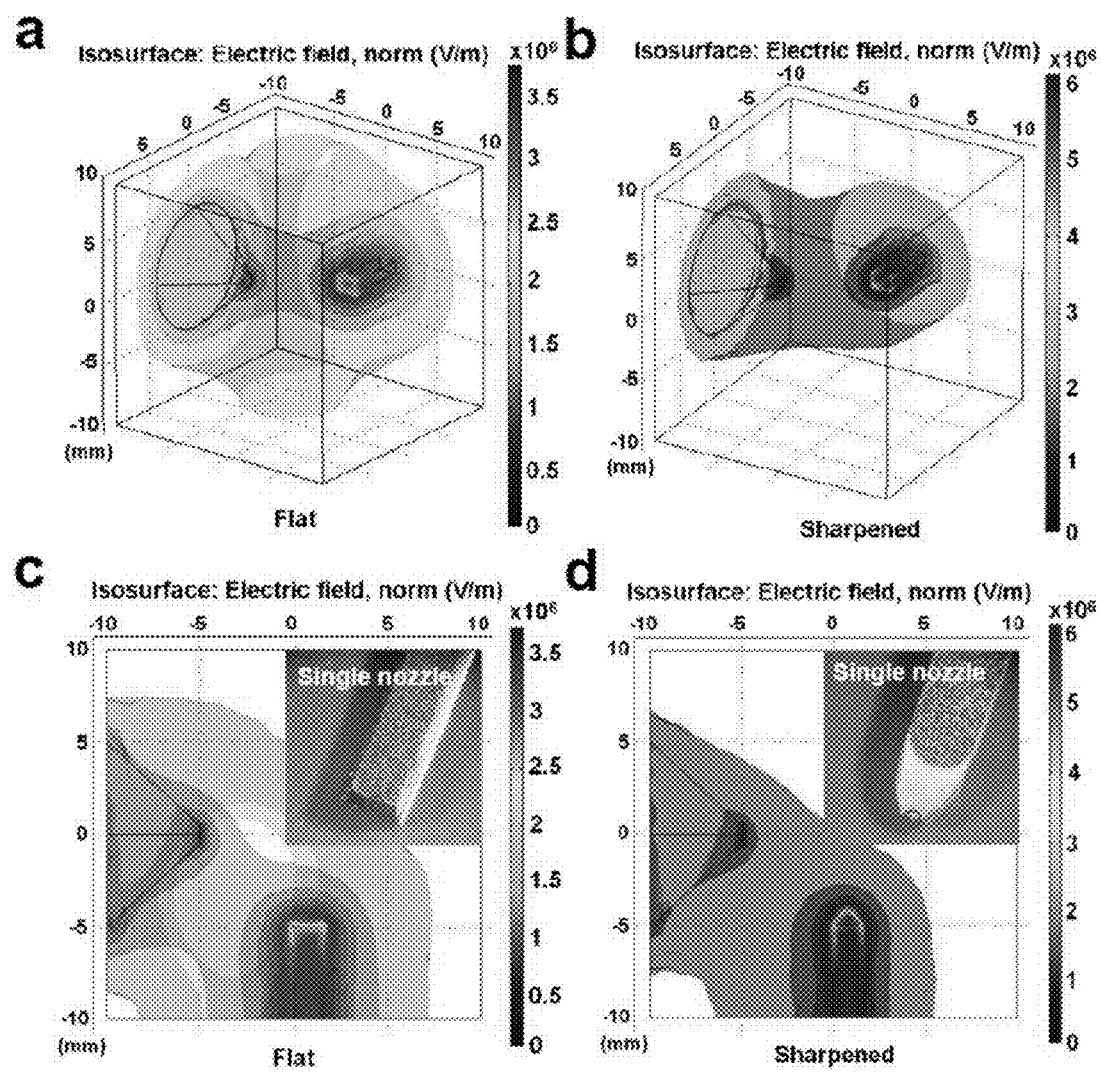
FIG. 10 shows electrostatic modeling for $M^3$ emitters. (a) 3D electric field models for simulated flat-end, and (b) sharpened-end $M^3$ emitters. Scale bar for the electric field is color-coded and shown on the right. Corresponding 2D top views are shown in (c) and (d), respectively. The insets in (c) and (d) are optical images of flat-end and sharpened-end single-nozzle $M^3$ emitter, with the circle in each inset indicating the single protruding nozzle.

We compared the electric field distribution between flat and sharpened $M^3$ emitters. FIGS. 10a and 10b show 3D views of simulated flat and sharpened emitters with respective electric fields. FIGS. 10c and 10d show corresponding plane views with inserts showing actual emitters with a single nozzle. We observed significant differences in both the strength and distribution of the electric fields. First, the magnitude of the field at the nozzle tip for sharpened $M^3$ emitter was about twice of that for flat emitters if the same voltage was applied, i.e., $2.8 \times 10^6$ (V/m) vs. $1.4 \times 10^6$ (V/m), for 3 kV at the emitters. Furthermore, the field was asymmetric for flat emitters, with clear edge effects at the four corners. By contrast, the field was more concentrated and evenly distributed at the nozzle region for sharpened emitters and only minimum edge effect was observed. Enhancement of electric fields at sharp tips is a known phenomenon for capillary-based single nozzle tips. However, ours is one of the first examples showing increased electric fields at the nozzles through sharpening the connecting microfabricated main channels instead of the nozzles themselves. Our modeling results suggested that a uniform and higher electric field can be achieved for the same operating voltage by sharpening the nozzle end of the $M^3$ emitters. It is expected that additional improvement could be achieved by optimizing the shape of the nozzle support and layout of the nozzles. The same modeling strategy could be adopted for future rational design of microfabricated ESI emitters and other components in complex microfluidic systems.

Fabrication of Sharpened $M^3$ Emitters with High-Density Nozzle Arrays.

Figure 11:
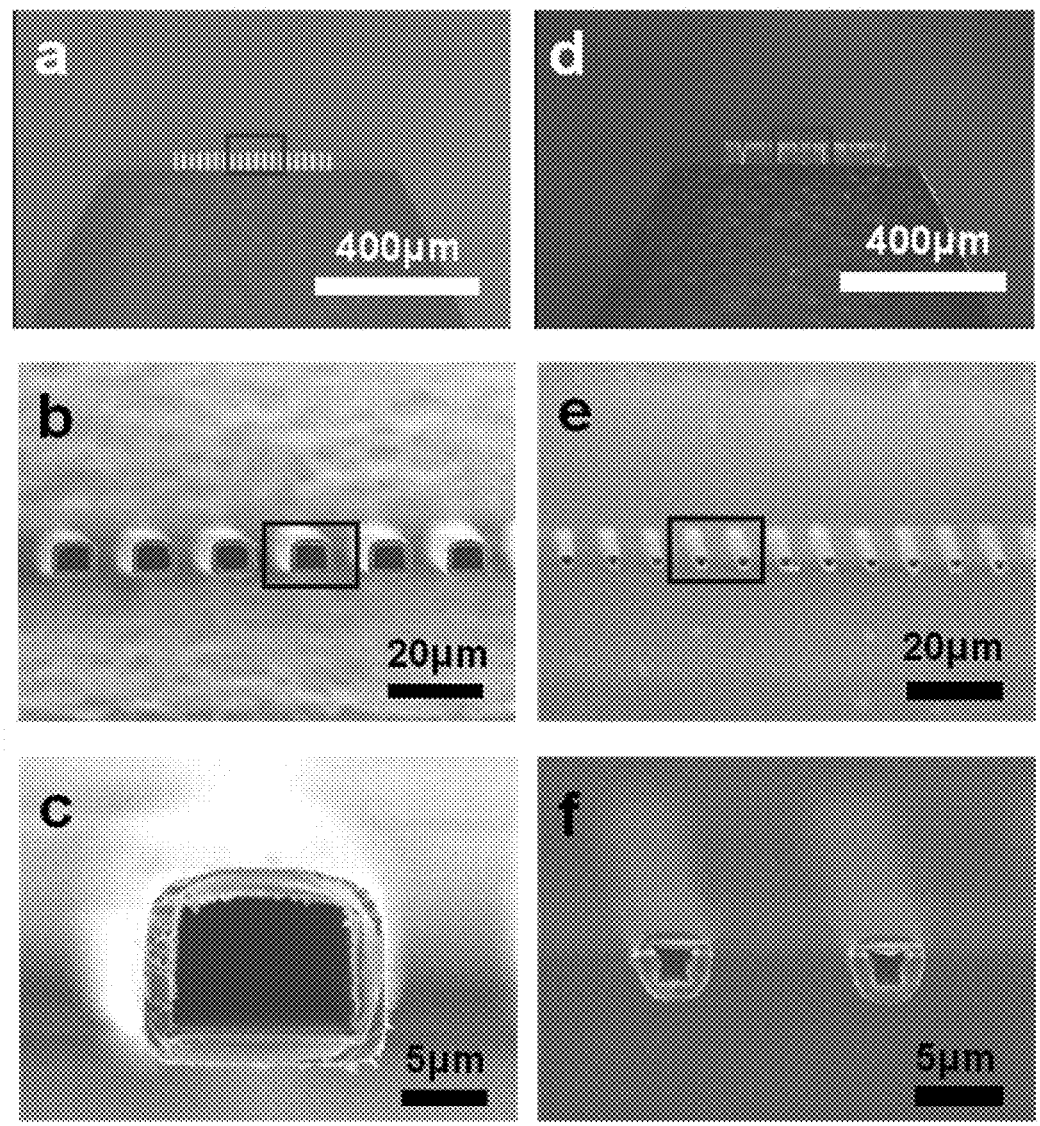
FIG. 11 shows optical and SEM images of sharpened $M^3$ emitters. (a) optical images of a 20-nozzle emitter; (b) SEM image of the nozzles highlighted in (a); (c) SEM image of the nozzle highlighted in (b); (d), (e), and (f) are corresponding images for a 40-nozzle emitter. Scale bars show 400 µm (a, d), 20 µm (b, e), and 5 µm (c, f), respectively.

We fabricated $M^3$ emitters with different numbers of nozzles, inter-nozzle spacing, and inner diameters of nozzles. FIG. 11 shows two representative sharpened emitters with multinozzles protruding from a main channel with a conduit width of 400 μm. FIG. 11a is the optical image of a 20-nozzle emitter. SEM images in FIG. 11b and its zoom-in in 11c demonstrated that the inter-nozzle spacing was ~10 μm, and the inner cross section (width×depth) was 10 μm×8 μm with a wall thickness of ~1.8 μm. Correspondingly, FIGS. 11d, 11e, and 11f show inter-nozzle spacing of ~8 μm, inner cross section of ~1.0×1.5 μm, and wall thickness of ~0.7 μm for a 40-nozzle emitter. The length of the nozzles (typically ~200 μm) could be varied depending on duration of the Si etching by $XeF_2$. We tested the $M^3$ emitters using organic solvents by direct infusion as we described previously[1]. As expected, there was a dramatic increase of back pressure once the cross section of each single nozzle was reduced from 10 μm×8 μm to 1.0×1.5 μm. This was consistent with ~10 times increase of pressure barrier (ΔP) for liquid leakage in microfluidic channels, as estimated by $\Delta P=-2\gamma \cos \theta \cdot (1/h+1/w)$; where γ and θ are surface tension of the liquid and the contact angle between the liquid and channel walls, respectively; while h and w are channel height and width, respectively[27]. Since the goal was to develop high-density $M^3$ emitters for LC-MS/MS applications in the present work, we tested the performance of $M^3$ emitters with a cross section of ~10 μm×8 μm in the following studies.

Nanoelectrospray Mass Spectrometry Using Sharpened $M^3$ Emitters.

We first confirmed that sharpening of the emitters dramatically reduced the operating voltage for electrospray ionization using a single-nozzle emitter. FIGS. 12a and 12b show voltage-dependent detection sensitivity of doubly-charged ions of GFP B (1 μM), quantified by the magnitude of the base peak intensity (BPI) for $[M+2H]^{2+}$ at 785.8 (m/z) per 2.4 second scan. Strikingly, optimal operating voltage was observed at 1.8 kV, which was even lower than those for commercial tips (2.1 kV~2.4 kV). This was a dramatic improvement over the flat-end single-nozzle $M^3$ emitters which required much higher voltage (4.5 kV~4.8 kV)[1]. Furthermore, we observed an increased sensitivity of 1,690 counts for sharpened emitters compared to around 1,000 counts for flat ones and conventional fused-silica capillary nanoelectrospary tips in the previous study. The sensitivity dependence on the voltage seemed to be dictated by the electrospray process. As shown in the inserts of FIG. 12a, a stream-like spray corresponding to "drip mode" was observed at 1.2 kV. A plume-like spray corresponding to "cone-jet mode" was clearly observed at 1.8 kV. Further increase of voltage resulted in "multi-jet mode" as exemplified at 3.0 kV.

The fundamental mechanism underlying the electrospray ionization (ESI) process remains controversial. Two competing models are the "charge residue model" proposed originally by Dole et al.[28], and the "ion evaporation model" proposed by Iribame and Thomson[29]. Despite their differences, both models support the notion that electrospray occurs while charged droplets reach the "Rayleigh limit" (the density of charges on the droplet surface increases to a critical value) and undergo Coulomb explosion while the droplets have radii R>10 nm. A "predominant fission pathways" model was proposed for nano-ESI[30, 31]. It suggested that nano-ESI produces a higher charge state of smaller initial droplets that decompose more promptly to offspring droplets from which ions are released. The process is presumably closer to the "ion-evaporation model" due to the very small droplets in the nano-ESI. Therefore, voltages applied to initial droplets and the resulting charge densities are critical in the ESI process. Future studies of our $M^3$ emitters using microscopes with high spatial and temporal resolutions will provide more insights into the dynamics of electro spray processes, and may provide new understanding of the mechanism underlying the ESI and nano-ESI.

Figure 13:
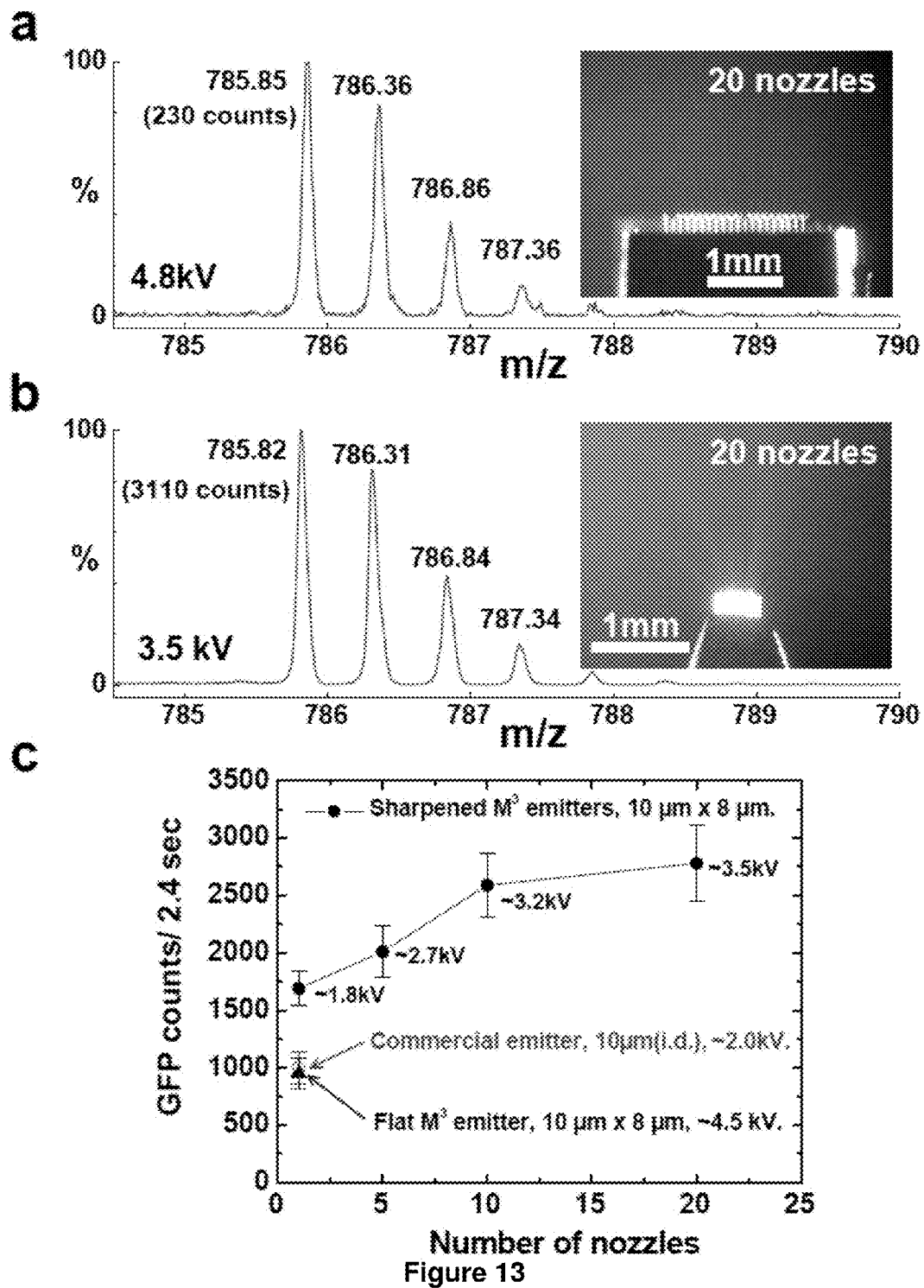
FIG. 13 shows nozzle number-dependent mass spectrometry sensitivity of sharpened $M^3$ emitters. (a) mass spectrum of 1 μM GFP B for a flat-end 20-nozzle emitter biased at 4.8 kV. (b) mass spectrum of 1 μM GFP B for a sharpened-end 20-nozzle emitter biased at 3.5 kV. The inserts show corresponding optical images of electrospray. Scale bar shows 1 mm. (c) mass spectrometry sensitivity of sharpened emitters with 1, 5, 10, 20 nozzles, as compared to that for a flat single-nozzle emitter and a conventional emitter. Standard deviation was calculated for a 10-minute scan under indicated optimal voltages.

We then compared the performance of flat and sharpened 20-nozzle emitters. As shown in FIG. 13a, flat emitters with inter-nozzle spacing of 90 μm produced a very weak GFP B signal (230 counts per scan) at 4.8 kV, corresponding to the "drip mode" (FIG. 13a insert). Decreasing inter-nozzle spacing to 10 μm resulted in the formation of a big droplet at the tip, caused by merge of small droplets coming out of each nozzle. This in term prevented the generation of stable electrospray. By contrast, a sharpened 20-nozzle emitter with inter-nozzle spacing of 10 μm generated strong a GFP B signal (3110 counts per scan) at 3.5 kV, corresponding to the cone-jet mode (FIG. 13b insert). The optimal voltage was 3.5 kV, higher than the 1.8 kV for the single-nozzle emitter (FIG. 12), suggesting aforementioned inter-nozzle interactions[25].

We next studied the dependence of optimal applied voltage and mass spectrometry sensitivity on nozzle numbers for sharpened emitters. As shown in FIG. 13c, both the optimal voltage and sensitivity increased with nozzle numbers. We observed a 3-fold increase on average for sharpened 20-nozzle emitters relative to commercial tips. However, the sensitivity for the 20-nozzle emitters was only 2-fold higher than that for sharpened single-nozzle ones (FIGS. 12 and 13c). A previous theoretical study of arrays of multiple capillary emitters (inner diameter ~150 μm, 1.1 mm apart) predicted MS sensitivity improvement by the square root of the number of nozzles[32]. If this holds for our sharpened multinozzle emitters, we would expect about 4.5-fold increase in this case. The sensitivity difference might be due to the stronger inter-nozzle interactions for our nozzles because of their much smaller cross sections and inter-nozzle spacing. Alternatively, it might be due to the suboptimal ion collecting efficiency resulting from the geometry constraint and inner diameter of the Z-spray sample cone of our mass spectrometer. Future optimization of nozzle number, nozzle diameter and inter-nozzle spacing for $M^3$ emitters, and mass spectrometry using funnel-shaped sample cone[22], may further increase the detection sensitivity for $M^3$ emitters with high-density nozzle arrays.

LC-MS/MS Using Sharpened M³ Emitters.

Figure 14:
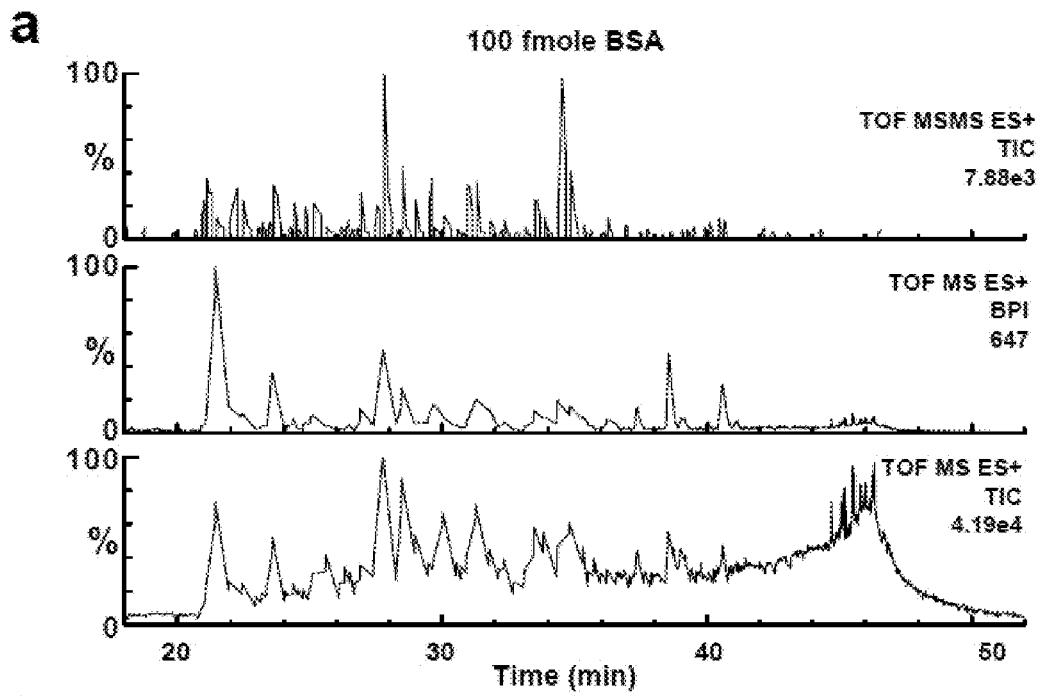
FIG. 14 shows protein identification using sharpened emitters. (a) representative LC-MS/MS spectra of 100 fmole tryptic digests of bovine serum albumin (BSA), showing total ion counts (TIC) and base peak intensity (BPI) for TOF MS, and TIC for TOF MS/MS (one trace out of three for data-dependent acquisition) over a 1-hour LC run. (b) identification of BSA through Mascot search of the MS/MS data in (a). Peptides sequenced are shown in red (SEQ ID NO:1).

We further demonstrated the applicability of these emitters in protein identification, which is critical for proteomics applications. FIG. 14a shows representative mass spectra of 100 fmole tryptic digests of bovine serum albumin (BSA, ~67 kDa), representing TOF MS (TIC), TOF MS (BPI), and TOF MS/MS (one trace out of three for DDA) over a 1 hr LC run. FIG. 14b shows the sequence coverage (in red) of BSA using Mascot search of the MS/MS data for sharpened M³ emitters. BSA was confidently identified with a Mowse score of 874, and 38% sequence coverage with 22 peptides sequenced. These results clearly showed that sharpened M³ emitters can be interfaced with LC-MS/MS for proteomics applications. Our next step is to pack the main channel of the M³ emitters with chromatography materials for protein and peptide separations. The resulting M³ emitters can serve as both a mini-column and an ESI emitter in lieu of a LC system. Furthermore, since these multinozzle emitters are microfabricated and monolithic, it is expected that they will serve as an integral component for $Si/SiO_2$ microfluidic systems to realize future proteomics-on-a-chip.

Conclusions

In summary, we presented the first demonstration of high-density microfabricated monolithic multinozzle emitters (M³ emitters). These sharpened multinozzle emitters showed reduced operating voltages yet increased detection sensitivity for nanoelectrospray mass spectrometry. Applications in protein identification demonstrated their potential as a key component for future $Si/SiO_2$-based systems for proteomics-on-a-chip.

REFERENCE (1) Kim, W.; Guo, M.; Yang, P.; Wang, D. *Anal Chem* 2007, 79, 3703-3707.
(2) Aebersold, R.; Mann, M. *Nature* 2003, 422, 198-207.
(3) Domon, B.; Aebersold, R. *Science* 2006, 312, 212-217.
(4) Fenn, J. B.; Mann, M.; Meng, C. K.; Wong, S. F.; Whitehouse, C. M. *Science* 1989, 246, 64-71.
(5) Wilm, M.; Mann, M. *Anal Chem* 1996, 68, 1-8.
(6) Mann, M.; Kelleher, N. L. *Proc Natl Acad Sci USA* 2008, 105, 18132-18138.
(7) Dittrich, P. S.; Tachikawa, K.; Manz, A. *Anal Chem* 2006, 78, 3887-3908.
(8) Whitesides, G. M. *Nature* 2006, 442, 368-373.
(9) DeMello, A. J. *Nature* 2006, 442, 394-402.
(10) El-Ali, J.; Sorger, P. K.; Jensen, K. F. *Nature* 2006, 442, 403-411.
(11) Huang, B.; Wu, H.; Bhaya, D.; Grossman, A.; Granier, S.; Kobilka, B. K.; Zare, R. N. *Science* 2007, 315, 81-84.
(12) Freire, S. L.; Wheeler, A. R. *Lab Chip* 2006, 6, 1415-1423.
(13) Koster, S.; Verpoorte, E. *Lab Chip* 2007, 7, 1394-1412.
(14) Licklider, L.; Wang, X. Q.; Desai, A.; Tai, Y. C.; Lee, T. D. *Anal Chem* 2000, 72, 367-375.
(15) Yang, Y.; Kameoka, J.; Wachs, T.; Henion, J. D.; Craighead, H. G. *Anal Chem* 2004, 76, 2568-2574.
(16) Kim, J. S.; Knapp, D. R. *J Am Soc Mass Spectrom* 2001, 12, 463-469.
(17) Schilling, M.; Nigge, W.; Rudzinski, A.; Neyer, A.; Hergenroder, R. *Lab Chip* 2004, 4, 220-224.
(18) Le Gac, S.; Cren-Olive, C.; Rolando, C.; Arscott, S. *J Am Soc Mass Spectrom* 2004, 15, 409-412.
(19) Schultz, G. A.; Corso, T. N.; Prosser, S. J.; Zhang, S. *Anal Chem* 2000, 72, 4058-4063.
(20) Lee, J. N.; Park, C.; Whitesides, G. M. *Anal Chem* 2003, 75, 6544-6554.
(21) Huang, B.; Wu, H.; Kim, S.; Zare, R. N. *Lab Chip* 2005, 5, 1005-1007.
(22) Kelly, R. T.; Page, J. S.; Zhao, R.; Qian, W. J.; Mottaz, H. M.; Tang, K.; Smith, R. D. *Anal Chem* 2008, 80, 143-149.
(23) Bocanegra, R.; Galan, D.; Marquez, M.; Loscertales, I. G.; Barrero, A. *J. Aerosol Sci.* 2005, 36, 1387-1399.
(24) Deng, W. W.; Klemic, J. F.; Li, X. H.; Reed, M. A.; Gomez, A. *J. Aerosol Sci.* 2006, 37, 696-714.
(25) Tatemoto, Y.; Ishikawa, R.; Takeuchi, M.; Takeshita, T.; Noda, K.; Okazaki, T. *Chem. Eng. Technol.* 2007, 30, 1274-1279.
(26) Wang, D.; Park, J. S.; Chu, J. S.; Krakowski, A.; Luo, K.; Chen, D. J.; Li, S. *J Biol Chem* 2004, 279, 43725-43734.
(27) Hosokawa, K.; Fujii, T.; Endo, I. *Anal Chem* 1999, 71, 4781-4785.
(28) Dole, M.; Mack, L. L.; Hines, R. L.; Mobley, R. C.; Ferguson, L. D.; Alice, M. B. *J Chem Phys* 1968, 49, 2240-2249.
(29) Iribarne, J. V.; Thomson, B. A. *J Chem Phys* 1976, 64, 2287-2294.
(30) Juraschek, R.; Dulcks, T.; Karas, M. *J Am Soc Mass Spectrom* 1999, 10, 300-308.
(31) Schmidt, A.; Karas, M.; Dulcks, T. *J Am Soc Mass Spectrom* 2003, 14, 492-500.
(32) Tang, K.; Lin, Y.; Matson, D. W.; Kim, T.; Smith, R. D. *Anal Chem* 2001, 73, 1658-1663.

Each of the references cited herein are hereby incorporated by reference as though each is individually incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A device comprising:
   a structure, the structure being circularly-shaped, a plurality of emitters defined on a circumference of the structure, a plurality of access holes defined in a first planar surface of the structure, a plurality of channels defined in the structure, each of the plurality of access holes being in fluid communication with one of the plurality of channels, each of the plurality of channels being in fluid communication with one of the plurality of emitters, a first emitter being defined by a top surface, a bottom surface, a left surface, a right surface, and an end surface, either the top surface and the bottom surface or the left surface and the right surface of the first emitter being sharpened to taper to the end surface; and
   a plurality of nozzles disposed in the end surface of each of the plurality of emitters, each of the plurality of nozzles protruding from the end surface of each of the plurality of emitters, the plurality of nozzles being in fluid communication with the channel of the emitter, and each of the plurality of nozzles including an end from which the nozzle is operable to emit a liquid.

2. The device of claim 1, wherein the structure comprises materials selected from a group consisting of silicon and glass.

3. The device of claim 1, wherein a first nozzle of the plurality of nozzles comprises a nanotube.

4. The device of claim 1, wherein the other of the top surface and the bottom surface or the left surface and the right surface of the first emitter are also sharpened to taper to the end surface to form a four-side sharpened end.

5. The device of claim 1, wherein the structure comprises ten or more emitters.

6. The device of claim 1, wherein a first emitter of the plurality of emitters includes ten or more nozzles disposed in the first emitter.

7. The device of claim 1, wherein an opening of a first nozzle of the plurality of nozzles has a cross-section with a longest linear dimension equal to or less than about 20 microns.

8. The device of claim 1, wherein the structure comprises a first silicon wafer and a second silicon wafer bonded to one another.

9. The device of claim 1, wherein each of the plurality of nozzles disposed in a second emitter of the plurality of emitters is disposed along a line.

10. The device of claim 1, wherein a first nozzle of the plurality of nozzles comprises $SiO_2$.

11. The device of claim 1, wherein a first nozzle of the plurality of nozzles has a cross-section that is an essentially circular shape or an essentially square shape.

12. The device of claim 1, wherein a first nozzle of the plurality of nozzles protrudes about 200 microns from one of the plurality of emitters.

13. The device of claim 1, wherein a first nozzle of the plurality of nozzles is defined by walls having a thickness of about 0.7 microns or about 1.8 microns.

14. The device of claim 1, wherein a first nozzle of the plurality of nozzles has a cross-section of about 2 microns to 10 microns by about 2 microns to 10 microns.

* * * * *